United States Patent
Lion et al.

(10) Patent No.: US 8,728,451 B2
(45) Date of Patent: May 20, 2014

(54) STYLING COMPOSITION COMPRISING, IN A PREDOMINANTLY AQUEOUS MEDIUM, A PSEUDO-BLOCK POLYMER, PROCESSES EMPLOYING SAME AND USES THEREOF

(75) Inventors: Bertrand Lion, Paris (FR); Katarina Benabdillah, Clichy (FR); Isabelle Rollat-Corvol, Paris (FR)

(73) Assignee: L'Oreal, Paris (FR)

( * ) Notice: Subject to any disclaimer, the term of this patent is extended or adjusted under 35 U.S.C. 154(b) by 1147 days.

(21) Appl. No.: 11/089,210

(22) Filed: Mar. 25, 2005

(65) Prior Publication Data

US 2005/0220747 A1    Oct. 6, 2005

Related U.S. Application Data

(60) Provisional application No. 60/571,925, filed on May 18, 2004.

(30) Foreign Application Priority Data

Mar. 25, 2004    (FR) .................................... 04 03090

(51) Int. Cl.
*A61Q 5/06*    (2006.01)

(52) U.S. Cl.
USPC ..................................................... 424/70.16

(58) Field of Classification Search
None
See application file for complete search history.

(56) References Cited

U.S. PATENT DOCUMENTS

| | | |
|---|---|---|
| 2,047,398 A | 7/1936 | Voss et al. |
| 2,528,378 A | 10/1950 | Mannheimer et al. |
| 2,723,248 A | 11/1955 | Wright |
| 2,781,354 A | 2/1957 | Mannheimer et al. |
| 3,673,160 A | 6/1972 | Buisson et al. |
| 3,716,633 A | 2/1973 | Viout et al. |
| 3,802,841 A | 4/1974 | Robin |
| 3,836,537 A | 9/1974 | Boerwinkle et al. |
| 3,910,862 A | 10/1975 | Barabas et al. |
| 3,915,921 A | 10/1975 | Schlatzer, Jr. |
| 3,925,542 A | 12/1975 | Viout et al. |
| 3,937,811 A | 2/1976 | Papantoniou et al. |
| 3,946,749 A | 3/1976 | Papantoniou |
| 3,966,403 A | 6/1976 | Papantoniou et al. |
| 3,966,404 A | 6/1976 | Papantoniou et al. |
| 3,990,459 A | 11/1976 | Papantoniou |
| 4,030,512 A | 6/1977 | Papantoniou et al. |
| 4,031,307 A | 6/1977 | DeMartino et al. |
| 4,032,628 A | 6/1977 | Papantoniou et al. |
| 4,070,533 A | 1/1978 | Papantoniou et al. |
| 4,076,912 A | 2/1978 | Papantoniou et al. |
| RE29,871 E | 12/1978 | Papantoniou et al. |
| 4,128,631 A | 12/1978 | Lundmark et al. |
| 4,129,711 A | 12/1978 | Viout et al. |
| 4,131,576 A | 12/1978 | Iovine |
| 4,137,208 A | 1/1979 | Elliott |
| 4,152,416 A | 5/1979 | Spitzer et al. |
| 4,165,367 A | 8/1979 | Chakrabarti |
| 4,223,009 A | 9/1980 | Chakrabarti |
| 4,282,203 A | 8/1981 | Jacquet et al. |
| 4,289,752 A | 9/1981 | Mahieu et al. |
| 4,425,326 A | 1/1984 | Guillon et al. |
| 4,509,949 A | 4/1985 | Huang et al. |
| 4,693,935 A | 9/1987 | Mazurek |
| 4,728,571 A | 3/1988 | Clemens et al. |
| 4,887,622 A | 12/1989 | Gueret |
| 4,972,037 A | 11/1990 | Garbe et al. |
| 4,981,902 A | 1/1991 | Mitra et al. |
| 4,981,903 A | 1/1991 | Garbe et al. |
| 5,000,937 A | 3/1991 | Grollier et al. |
| 5,061,481 A | 10/1991 | Suzuki et al. |
| 5,110,582 A | 5/1992 | Hungerbuhler et al. |
| 5,156,911 A | 10/1992 | Stewart |
| 5,209,924 A | 5/1993 | Garbe et al. |
| 5,219,560 A | 6/1993 | Suzuki et al. |
| 5,266,321 A | 11/1993 | Shukuzaki |
| 5,362,485 A | 11/1994 | Hayama et al. |
| 5,391,631 A | 2/1995 | Porsch et al. |
| 5,468,477 A | 11/1995 | Kumar et al. |
| 5,472,798 A | 12/1995 | Kumazawa et al. |
| 5,492,426 A | 2/1996 | Gueret |
| 5,519,063 A | 5/1996 | Mondet et al. |
| 5,538,717 A | 7/1996 | De La Poterie |
| 5,681,877 A | 10/1997 | Hosotte-Filbert et al. |
| 5,686,067 A | 11/1997 | Shih et al. |
| 5,690,918 A | 11/1997 | Jacks et al. |
| 5,711,940 A | 1/1998 | Kuentz et al. |

(Continued)

FOREIGN PATENT DOCUMENTS

| | | |
|---|---|---|
| DE | 2 330 956 | 1/1974 |
| DE | 100 22 247 | 11/2001 |

(Continued)

OTHER PUBLICATIONS

Porter, "Ch. 7 Non-ionics," *Handbook of Surfactants*, 1991, pp. 116-178, Chapman and Hall, New York.
Fonnum et al., Colloid Polym. Sci , 1993, 271:380-389.
French Search Report of FR Patent Application No. 0 403 090, dated Sep. 30, 2004.
Aldrich: Polymer Properties; 4th Ed. Catalog No. Z41, 247-3 (1999) published by John Wiley, New York.
Boutevin, B. et al., "Study of Morphological and Mechanical Properties of PP/PBT," Polymer Bulletin, 34, pp. 117-123, (1995).
Buzin, A. et al., "Calorimetric Study of Block-Copolymers of Poly(n-butyl Acrylate) and Gradient Poly(n-butyl acrylate-co-methyl methacrylate)" vol. 43, 2002, pp. 5563-5569.

(Continued)

*Primary Examiner* — Jyothsna Venkat
(74) *Attorney, Agent, or Firm* — O'Brien Jones, PLLC

(57) ABSTRACT

The disclosure provides styling cosmetic compositions comprising, in a cosmetically acceptable medium predominantly comprising water, at least one pseudo-block polymer, cosmetic treatment processes for shaping and/or holding the hairstyle employing the cosmetic compositions and also to uses of the cosmetic compositions for obtaining shaping of the hair that is persistent over time and shaping of the hair that is moisture-resistant.

16 Claims, No Drawings

(56) References Cited

U.S. PATENT DOCUMENTS

| | | |
|---|---|---|
| 5,725,882 A | 3/1998 | Kumar et al. |
| 5,736,125 A | 4/1998 | Morawsky et al. |
| 5,747,013 A | 5/1998 | Mougin et al. |
| 5,756,635 A | 5/1998 | Michaud et al. |
| 5,772,347 A | 6/1998 | Gueret |
| 5,783,657 A | 7/1998 | Pavlin et al. |
| 5,807,540 A | 9/1998 | Junino et al. |
| 5,849,275 A | 12/1998 | Calello et al. |
| 5,849,318 A | 12/1998 | Imai et al. |
| 5,879,095 A | 3/1999 | Gueret |
| 5,897,870 A | 4/1999 | Schehlmann et al. |
| 5,948,393 A | 9/1999 | Tomomasa et al. |
| 5,994,446 A | 11/1999 | Graulus et al. |
| 6,001,367 A | 12/1999 | Bazin et al. |
| 6,001,374 A | 12/1999 | Nichols |
| 6,027,739 A | 2/2000 | Nichols |
| 6,033,650 A | 3/2000 | Calello et al. |
| 6,059,473 A | 5/2000 | Gueret |
| 6,074,654 A | 6/2000 | Drechsler et al. |
| 6,083,516 A | 7/2000 | Curtis et al. |
| 6,106,813 A | 8/2000 | Mondet et al. |
| 6,106,820 A | 8/2000 | Morrissey et al. |
| 6,120,781 A | 9/2000 | Le Bras et al. |
| 6,126,929 A | 10/2000 | Mougin |
| 6,132,742 A | 10/2000 | Le Bras et al. |
| 6,139,849 A | 10/2000 | Lesaulnier et al. |
| 6,140,431 A | 10/2000 | Kinker et al. |
| 6,153,206 A | 11/2000 | Anton et al. |
| 6,156,804 A | 12/2000 | Chevalier et al. |
| 6,160,054 A | 12/2000 | Schwindeman et al. |
| 6,165,457 A | 12/2000 | Midha et al. |
| 6,166,093 A | 12/2000 | Mougin et al. |
| 6,174,968 B1 | 1/2001 | Hoxmeier |
| 6,180,123 B1 | 1/2001 | Mondet |
| 6,197,883 B1 | 3/2001 | Schimmel et al. |
| 6,225,390 B1 | 5/2001 | Hoxmeier |
| 6,228,946 B1 | 5/2001 | Kitayama et al. |
| 6,228,967 B1 | 5/2001 | Fost et al. |
| 6,238,679 B1 | 5/2001 | De La Poterie et al. |
| 6,254,878 B1 | 7/2001 | Bednarek et al. |
| 6,258,916 B1 | 7/2001 | Michaud et al. |
| 6,267,951 B1 | 7/2001 | Shah et al. |
| 6,268,466 B1 | 7/2001 | MacQueen et al. |
| 6,280,713 B1 | 8/2001 | Tranchant et al. |
| 6,303,105 B1 | 10/2001 | Shah et al. |
| 6,319,959 B1 | 11/2001 | Mougin et al. |
| 6,326,011 B1 | 12/2001 | Miyazawa et al. |
| 6,328,495 B1 | 12/2001 | Gueret |
| 6,342,237 B1 | 1/2002 | Bara |
| 6,372,876 B1 | 4/2002 | Kim et al. |
| 6,386,781 B1 | 5/2002 | Gueret |
| 6,395,265 B1 | 5/2002 | Mougin et al. |
| 6,399,691 B1 | 6/2002 | Melchiors et al. |
| 6,410,005 B1 * | 6/2002 | Galleguillos et al. ...... 424/70.16 |
| 6,410,666 B1 | 6/2002 | Grubbs et al. |
| 6,412,496 B1 | 7/2002 | Gueret |
| 6,423,306 B2 | 7/2002 | Caes et al. |
| 6,464,969 B2 | 10/2002 | De La Poterie et al. |
| 6,484,731 B1 | 11/2002 | Lacout |
| 6,491,927 B1 | 12/2002 | Arnaud et al. |
| 6,518,364 B2 | 2/2003 | Charmot et al. |
| 6,531,535 B2 | 3/2003 | Melchiors et al. |
| 6,552,146 B1 | 4/2003 | Mougin |
| 6,581,610 B1 | 6/2003 | Gueret |
| 6,649,173 B1 | 11/2003 | Arnaud et al. |
| 6,663,855 B2 | 12/2003 | Frechet et al. |
| 6,663,885 B1 | 12/2003 | Hager et al. |
| 6,685,925 B2 | 2/2004 | Frechet et al. |
| 6,692,173 B2 | 2/2004 | Gueret |
| 6,692,733 B1 | 2/2004 | Mougin |
| 6,770,271 B2 | 8/2004 | Mondet et al. |
| 6,805,872 B2 | 10/2004 | Mougin |
| 6,833,419 B2 | 12/2004 | Morschhauser et al. |
| 6,843,611 B2 | 1/2005 | Blondeel et al. |
| 6,866,046 B2 | 3/2005 | Gueret |
| 6,881,780 B2 | 4/2005 | Bryant et al. |
| 6,890,522 B2 | 5/2005 | Frechet et al. |
| 6,891,011 B2 | 5/2005 | Morschhauser et al. |
| 6,905,696 B2 | 6/2005 | Marotta et al. |
| 6,946,518 B2 | 9/2005 | De La Poterie |
| 6,960,339 B1 | 11/2005 | Ferrari |
| 6,964,995 B2 | 11/2005 | Morschhauser et al. |
| 7,022,791 B2 | 4/2006 | Loffler et al. |
| 7,025,973 B2 | 4/2006 | Loffler et al. |
| 7,053,146 B2 | 5/2006 | Morschhauser et al. |
| 7,081,507 B2 | 7/2006 | Morschhauser et al. |
| 7,144,171 B2 | 12/2006 | Blondeel et al. |
| 7,151,137 B2 | 12/2006 | Morschhauser et al. |
| 7,176,170 B2 | 2/2007 | Dubief et al. |
| 7,186,405 B2 | 3/2007 | Loeffler et al. |
| 7,186,774 B2 | 3/2007 | Morschhauser et al. |
| 7,244,421 B2 | 7/2007 | Loffler et al. |
| 7,279,154 B2 | 10/2007 | Loffler et al. |
| 7,297,328 B2 | 11/2007 | Loffler et al. |
| 7,332,155 B2 | 2/2008 | Loffler et al. |
| 7,358,303 B2 | 4/2008 | De La Poterie |
| 7,393,520 B2 | 7/2008 | Loeffler et al. |
| 7,399,478 B2 | 7/2008 | Loffler et al. |
| 7,803,877 B2 * | 9/2010 | Lion et al. ...................... 525/301 |
| 7,915,347 B2 | 3/2011 | Lion et al. |
| 7,932,324 B2 | 4/2011 | Lion et al. |
| 2002/0015611 A1 | 2/2002 | Blondeel et al. |
| 2002/0018759 A1 | 2/2002 | Pagano et al. |
| 2002/0020424 A1 | 2/2002 | Gueret |
| 2002/0035237 A1 | 3/2002 | Lawson et al. |
| 2002/0054783 A1 | 5/2002 | Gueret |
| 2002/0055562 A1 | 5/2002 | Butuc |
| 2002/0061319 A1 | 5/2002 | Bernard et al. |
| 2002/0064539 A1 | 5/2002 | Philippe et al. |
| 2002/0076390 A1 | 6/2002 | Kantner et al. |
| 2002/0076425 A1 | 6/2002 | Mondet et al. |
| 2002/0098217 A1 | 7/2002 | Piot et al. |
| 2002/0115780 A1 | 8/2002 | Mougin |
| 2002/0150546 A1 | 10/2002 | Mougin et al. |
| 2002/0151638 A1 | 10/2002 | Melchiors et al. |
| 2002/0159965 A1 | 10/2002 | Frechet et al. |
| 2002/0160026 A1 | 10/2002 | Frechet et al. |
| 2003/0003154 A1 | 1/2003 | De La Poterie |
| 2003/0017124 A1 | 1/2003 | Agostini et al. |
| 2003/0017182 A1 | 1/2003 | Tournilhac |
| 2003/0021815 A9 | 1/2003 | Mondet et al. |
| 2003/0024074 A1 | 2/2003 | Hartman |
| 2003/0039621 A1 | 2/2003 | Arnaud et al. |
| 2003/0059392 A1 | 3/2003 | L'Alloret |
| 2003/0113285 A1 | 6/2003 | Meffert et al. |
| 2003/0124074 A1 | 7/2003 | Mougin et al. |
| 2003/0124079 A1 | 7/2003 | Mougin et al. |
| 2003/0185774 A1 | 10/2003 | Dobbs et al. |
| 2003/0191271 A1 | 10/2003 | Mondet et al. |
| 2004/0009136 A1 | 1/2004 | Dubief et al. |
| 2004/0013625 A1 | 1/2004 | Kanji |
| 2004/0014872 A1 | 1/2004 | Raether |
| 2004/0039101 A1 | 2/2004 | Dubief et al. |
| 2004/0052745 A1 | 3/2004 | Bernard et al. |
| 2004/0052752 A1 | 3/2004 | Samain et al. |
| 2004/0077788 A1 | 4/2004 | Guerra et al. |
| 2004/0091444 A1 | 5/2004 | Loffler et al. |
| 2004/0093676 A1 | 5/2004 | Vidal et al. |
| 2004/0096409 A1 | 5/2004 | Loeffler et al. |
| 2004/0096411 A1 | 5/2004 | Frechet et al. |
| 2004/0097657 A1 | 5/2004 | Morschhaeuser et al. |
| 2004/0109835 A1 | 6/2004 | Loffler et al. |
| 2004/0109836 A1 | 6/2004 | Loffler et al. |
| 2004/0109838 A1 | 6/2004 | Morschhauser et al. |
| 2004/0115148 A1 | 6/2004 | Loffler et al. |
| 2004/0115149 A1 | 6/2004 | Loffler et al. |
| 2004/0115157 A1 | 6/2004 | Loffler et al. |
| 2004/0116628 A1 | 6/2004 | Morschhauser et al. |
| 2004/0116634 A1 | 6/2004 | Morschhaeuser et al. |
| 2004/0120906 A1 * | 6/2004 | Toumi et al. ................... 424/61 |
| 2004/0120920 A1 | 6/2004 | Lion et al. |
| 2004/0137020 A1 | 7/2004 | De La Poterie et al. |
| 2004/0137021 A1 | 7/2004 | De La Poterie et al. |
| 2004/0141937 A1 | 7/2004 | Loffler et al. |

(56) References Cited

U.S. PATENT DOCUMENTS

| | | |
|---|---|---|
| 2004/0141943 A1 | 7/2004 | Mougin et al. |
| 2004/0142831 A1 | 7/2004 | Jager Lezer |
| 2004/0167304 A1 | 8/2004 | Morschhauser et al. |
| 2004/0223933 A1 | 11/2004 | Hiwatashi et al. |
| 2004/0241118 A1 | 12/2004 | Simon et al. |
| 2005/0002724 A1 | 1/2005 | Blondeel et al. |
| 2005/0020779 A1 | 1/2005 | Mougin et al. |
| 2005/0032998 A1 | 2/2005 | Morschhauser et al. |
| 2005/0089536 A1 | 4/2005 | Loffler et al. |
| 2005/0095213 A1 | 5/2005 | Blin et al. |
| 2005/0106197 A1 | 5/2005 | Blin et al. |
| 2005/0129641 A1 | 6/2005 | Arnaud et al. |
| 2005/0201958 A1 | 9/2005 | De La Poterie |
| 2005/0220731 A1 | 10/2005 | Ilekti et al. |
| 2005/0220747 A1 | 10/2005 | Lion et al. |
| 2005/0232887 A1 | 10/2005 | Morschhauser et al. |
| 2005/0287103 A1 | 12/2005 | Filippi et al. |
| 2006/0093568 A1 | 5/2006 | Blin et al. |
| 2006/0099164 A1* | 5/2006 | De La Poterie et al. ..... 424/70.1 |
| 2006/0099231 A1 | 5/2006 | De La Poterie et al. |
| 2006/0115444 A1 | 6/2006 | Blin et al. |
| 2006/0127334 A1* | 6/2006 | Ferrari et al. ................ 424/64 |
| 2006/0134032 A1* | 6/2006 | Ilekti et al. ................... 424/61 |
| 2006/0134034 A1 | 6/2006 | Blin et al. |
| 2006/0134038 A1 | 6/2006 | De La Poterie et al. |
| 2006/0134044 A1 | 6/2006 | Blin et al. |
| 2006/0134051 A1 | 6/2006 | Blin et al. |
| 2006/0147402 A1 | 7/2006 | Blin et al. |
| 2006/0147403 A1* | 7/2006 | Ferrari et al. ............. 424/70.16 |
| 2007/0003506 A1 | 1/2007 | Mougin et al. |
| 2007/0003507 A1 | 1/2007 | Mougin et al. |
| 2007/0166259 A1 | 7/2007 | Vicic et al. |
| 2008/0014158 A1* | 1/2008 | Lion et al. ..................... 424/59 |
| 2008/0014232 A1 | 1/2008 | Arnaud et al. |
| 2008/0014234 A1 | 1/2008 | Lion et al. |
| 2008/0014235 A1 | 1/2008 | Lion et al. |
| 2008/0050329 A1 | 2/2008 | De La Poterie |
| 2008/0069793 A1 | 3/2008 | Loffler et al. |
| 2008/0107617 A1 | 5/2008 | Loffler et al. |
| 2008/0159965 A1 | 7/2008 | Mougin et al. |
| 2008/0207773 A1 | 8/2008 | Loffler et al. |
| 2008/0219943 A1 | 9/2008 | De La Poterie |

FOREIGN PATENT DOCUMENTS

| | | |
|---|---|---|
| DE | 100 29 697 | 12/2001 |
| EP | 1 279 398 | 9/1971 |
| EP | 0 295 886 | 12/1988 |
| EP | 0 320 218 A2 | 6/1989 |
| EP | 0 173 109 B1 | 10/1989 |
| EP | 0 388 582 | 9/1990 |
| EP | 0 412 704 | 2/1991 |
| EP | 0 412 707 | 2/1991 |
| EP | 0 549 494 | 6/1993 |
| EP | 0 582 152 | 2/1994 |
| EP | 0 216 479 B2 | 8/1994 |
| EP | 0 619 111 | 10/1994 |
| EP | 0 637 600 | 2/1995 |
| EP | 0 648 485 | 4/1995 |
| EP | 0 656 021 | 6/1995 |
| EP | 0 667 146 | 8/1995 |
| EP | 0 550 745 | 9/1995 |
| EP | 0 686 858 | 12/1995 |
| EP | 0 750 031 | 12/1996 |
| EP | 0 751 162 | 1/1997 |
| EP | 0 751 170 | 1/1997 |
| EP | 0 847 752 | 6/1998 |
| EP | 0 861 859 | 9/1998 |
| EP | 0 951 897 | 10/1999 |
| EP | 1 018 311 | 7/2000 |
| EP | 1 024 184 | 8/2000 |
| EP | 1 043 345 | 10/2000 |
| EP | 1 066 817 | 1/2001 |
| EP | 1 068 856 | 1/2001 |
| EP | 1 192 930 | 4/2002 |
| EP | 1 201 221 | 5/2002 |
| EP | 1 356 799 | 10/2003 |
| EP | 1 366 741 | 12/2003 |
| EP | 1 366 744 | 12/2003 |
| EP | 1 366 746 | 12/2003 |
| EP | 1 411 069 | 4/2004 |
| EP | 0 955 039 | 5/2004 |
| EP | 1 421 928 | 5/2004 |
| EP | 1 440 680 | 7/2004 |
| EP | 1 518 534 | 3/2005 |
| EP | 1 518 535 | 3/2005 |
| EP | 1 604 634 | 12/2005 |
| FR | 1 222 944 | 6/1960 |
| FR | 1 400 366 | 4/1965 |
| FR | 1 564 110 | 3/1969 |
| FR | 1 580 545 | 9/1969 |
| FR | 2 077 143 | 9/1971 |
| FR | 2 079 785 | 11/1971 |
| FR | 2 232 303 | 1/1975 |
| FR | 2 265 781 | 10/1975 |
| FR | 2 265 782 | 10/1975 |
| FR | 2 350 384 | 12/1977 |
| FR | 2 357 241 | 2/1978 |
| FR | 2 393 573 | 1/1979 |
| FR | 2 439 798 | 5/1980 |
| FR | 2 710 646 | 4/1995 |
| FR | 2 722 380 | 6/1996 |
| FR | 2 727 609 | 6/1996 |
| FR | 2 743 297 | 7/1997 |
| FR | 2 761 959 | 10/1998 |
| FR | 2 796 529 | 7/1999 |
| FR | 2 775 566 | 9/1999 |
| FR | 2 775 593 | 9/1999 |
| FR | 2 791 042 | 9/2000 |
| FR | 2 791 988 | 10/2000 |
| FR | 2 792 618 | 10/2000 |
| FR | 2 806 273 | 9/2001 |
| FR | 2 296 402 | 11/2001 |
| FR | 2 809 306 | 11/2001 |
| FR | 2 811 993 | 1/2002 |
| FR | 2 814 365 | 3/2002 |
| FR | 2 816 503 | 5/2002 |
| FR | 2 823 101 | 10/2002 |
| FR | 2 823 103 | 10/2002 |
| FR | 2 827 514 | 1/2003 |
| FR | 2 831 430 | 5/2003 |
| FR | 2 840 205 | 12/2003 |
| FR | 2 840 209 | 12/2003 |
| FR | 2 842 417 | 1/2004 |
| FR | 2 844 709 | 3/2004 |
| FR | 2 860 143 | 4/2005 |
| FR | 2 880 268 | 7/2006 |
| GB | 0 839 805 | 6/1960 |
| GB | 0 922 457 | 4/1963 |
| GB | 1 021 400 | 3/1966 |
| GB | 1 169 862 | 11/1969 |
| GB | 1 324 745 | 7/1973 |
| GB | 1 331 819 | 9/1973 |
| GB | 1 407 659 | 9/1975 |
| GB | 1 572 626 | 7/1980 |
| JP | 07-324017 | 12/1995 |
| JP | 10-506404 | 6/1998 |
| JP | 2000-83728 | 3/2000 |
| JP | 2000-319325 | 11/2000 |
| JP | 2000-319326 | 11/2000 |
| JP | 2001-527559 | 12/2001 |
| JP | 2002-201110 | 7/2002 |
| JP | 2003-40336 | 2/2003 |
| JP | 2003-73222 | 3/2003 |
| JP | 2003-081742 | 3/2003 |
| JP | 2003-286142 | 10/2003 |
| JP | 2004-149772 | 5/2004 |
| JP | 2004-269497 | 9/2004 |
| JP | 2005-104979 | 4/2005 |
| JP | 2006-503921 | 3/2006 |
| JP | 2006-507355 | 3/2006 |
| JP | 2006-507365 | 3/2006 |
| JP | 2006-507366 | 3/2006 |

(56) References Cited

FOREIGN PATENT DOCUMENTS

| | | |
|---|---|---|
| JP | 2006-507367 | 3/2006 |
| JP | 2006-151867 | 6/2006 |
| LU | 75370 | 7/1976 |
| LU | 75371 | 7/1976 |
| WO | WO 93/01797 | 2/1993 |
| WO | WO 93/23009 | 11/1993 |
| WO | WO 93/23446 | 11/1993 |
| WO | WO 94/03510 | 2/1994 |
| WO | WO 95/00578 | 1/1995 |
| WO | WO 95/03776 | 2/1995 |
| WO | WO 95/06078 | 3/1995 |
| WO | WO 96/10044 | 4/1996 |
| WO | WO 97/17057 | 5/1997 |
| WO | WO 98/31329 | 7/1998 |
| WO | WO 98/38981 | 9/1998 |
| WO | WO 98/42298 | 10/1998 |
| WO | WO 98/44012 | 10/1998 |
| WO | WO 98/51276 | 11/1998 |
| WO | WO 00/26285 | 5/2000 |
| WO | WO 00/28948 | 5/2000 |
| WO | WO 00/40216 | 7/2000 |
| WO | WO 00/49997 | 8/2000 |
| WO | WO 01/19333 | 3/2001 |
| WO | WO 01/30886 | 5/2001 |
| WO | WO 01/43703 | 6/2001 |
| WO | WO 01/89470 | 11/2001 |
| WO | WO 01/95871 | 12/2001 |
| WO | WO 02/05762 | 1/2002 |
| WO | WO 02/05765 | 1/2002 |
| WO | WO 02/028358 | 4/2002 |
| WO | WO 02/34218 | 5/2002 |
| WO | WO 02/067877 | 9/2002 |
| WO | WO 02/080869 | 10/2002 |
| WO | WO 03/018423 | 3/2003 |
| WO | WO 03/046032 | 6/2003 |
| WO | WO 03/046033 | 6/2003 |
| WO | WO 2004/022009 | 3/2004 |
| WO | WO 2004/022010 | 3/2004 |
| WO | WO 2004/024700 | 3/2004 |
| WO | WO 2004/028489 | 4/2004 |
| WO | WO 2005/030158 | 4/2005 |

OTHER PUBLICATIONS

Co-pending U.S. Appl. No. 10/528,698, filed Mar. 22, 2005; Inventors: Veronique Ferrari et al.
Co-pending U.S. Appl. No. 10/528,699, filed Mar. 22, 2005; Inventors: Philippe Ilekti et al.
Co-pending U.S. Appl. No. 10/528,835, filed Mar. 23, 2005; Inventors: Xavier Blin et al.
Co-pending U.S. Appl. No. 10/529,218, filed Mar. 25, 2005; Inventors: Xavier Blin et al.
Co-pending U.S. Appl. No. 10/529,264, filed Mar. 25, 2005; Inventors: Veronique Ferrari et al.
Co-pending U.S. Appl. No. 10/529,265, filed Sep. 28, 2005; Inventors: Xavier Blin et al.
Co-pending U.S. Appl. No. 10/529,266, filed Mar. 25, 2005; Inventors: Xavier Blin et al.
Co-pending U.S. Appl. No. 10/529,267, filed Sep. 29, 2005; Inventors: Valerie De La Poterie et al.
Co-pending U.S. Appl. No. 10/529,318, filed Mar. 25, 2005; Inventors: Xavier Blin et al.
Co-pending U.S. Appl. No. 10/573,579; filed Dec. 26, 2006; Inventor: Marco Vicic et al.
Co-pending U.S. Appl. No. 10/585,817, filed Jan. 10, 2007; Inventor: Valerie De La Poterie.
Co-pending U.S. Appl. No. 10/585,818, filed Jul. 12, 2006; Inventors: Valerie De La Poterie.
Co-pending U.S. Appl. No. 10/670,388, filed Sep. 26, 2003; Inventors: Beatrice Toumi et al.
Co-pending U.S. Appl. No. 10/670,478, filed Sep. 26, 2003; Inventors: Bertrand Lion et al.
Co-pending U.S. Appl. No. 10/949,448, filed Sep. 27, 2004; Inventors: Xavier Blin et al.
Co-pending U.S. Appl. No. 11/086,906, filed Mar. 23, 2005; Inventors: Philippe Ilekti et al.
Co-pending U.S. Appl. No. 11/858,994, filed Sep. 21, 2007; Inventors: Bertrand Lion et al.
Co-pending U.S. Appl. No. 11/859,004, filed Sep. 21, 2007; Inventors: Bertrand Lion et al.
Co-pending U.S. Appl. No. 11/859,015, filed Sep. 21, 2007; Inventors: Bertrand Lion et al.
English Derwent Abstract for EP 1 082 953, dated Mar. 14, 2001.
English Derwent Abstract for EP 1 159 950, dated Dec. 5, 2001.
English Derwent Abstract for FR 2 798 061, dated Mar. 9, 2001.
English Derwent Abstract for FR 2 803 743, dated Jul. 20, 2001.
English Derwent Abstract for FR 2 832 719, dated May 30, 2003.
English Derwent Abstract for WO 01/03538, dated Jan. 18, 2001.
English Derwent Abstract for WO 04/028489, dated Apr. 8, 2004.
English language Abstract of FR 2 710 552, dated Apr. 7, 1995.
English language Abstract of FR 2 710 646, dated Apr. 7, 1995.
English language Abstract of FR 2 791 987, dated Oct. 13, 2000.
English language Abstract of FR 2 832 720, dated May 30, 2003.
English language Abstract of FR 2 834 458, dated Jul. 11, 2003.
English language Abstract of JP 07-309721, dated Nov. 28, 1995.
English language Abstract of JP 08-119836, dated May 14, 1996.
English language Abstract of WO 01/13863, dated Mar. 1, 2001.
English language Abstract of WO 01/51018, dated Jul. 19, 2001.
English language Derwent Abstract for EP 0 080 976, dated Jun. 8, 1983.
English language Derwent Abstract for EP 0 815 836, dated Jan. 7, 1998.
English language Derwent Abstract for FR 2 775 566, dated Sep. 10, 1999.
English language Derwent Abstract for FR 2 792 190, dated Oct. 20, 2000.
English language Derwent Abstract for FR 2 831 430, dated May 2, 2003.
English language Derwent Abstract for JP 06-279323, dated Oct. 4, 1994.
English language Derwent Abstract for JP 07-196450, dated Aug. 1, 1995.
English language Derwent Abstract for JP 09-263518, dated Oct. 7, 1997.
English language Derwent Abstract for JP 11-124312, dated May 11, 1999.
English language Derwent Abstract of DE 100 29 697, dated Dec. 20, 2001.
English language Derwent Abstract of EP 0 648 485, dated Apr. 19, 1995.
English language Derwent Abstract of FR 2 140 977, dated Jan. 19, 1973.
English language Derwent Abstract of FR 2 860 156, dated Apr. 1, 2005.
English language Derwent Abstract of JP 11-100307, dated Apr. 13, 1999.
English language Derwent Abstract of JP 2001-348553, dated Dec. 18, 2001.
English language Derwent Abstract of JP 2002-201244, dated Jul. 19, 2002.
English language Derwent Abstract of JP 2004-002432, dated Jan. 8, 2004.
English language Derwent Abstract of JP 2004-002435, dated Jan. 8, 2004.
English language Derwent Abstract of JP 5-221829, dated Aug. 31, 1993.
European Search Report for EP 03 29 2383, dated May 17, 2004, in Co-pending U.S. Appl. No. 10/670,388.
Flick, "Cosmetic Additives: An Industrial Guide", Noyes Publications, Park Ridge, NJ, p. 266 (1991).
French Search Report for FR 02/11949 for Copending U.S. Appl. No. 10/670,478, dated Jul. 7, 2003.
French Search Report for FR 03/11340 for Copending U.S. Appl. No. 10/949,448, dated May 9, 2005.
French Search Report for FR 04/50572, for Copending U.S. Appl. No. 11/086,906, dated Nov. 9, 2004.

(56) References Cited

OTHER PUBLICATIONS

Hamley, I.W., "Crystallization in Block Copolymers," Advances in Polymer Science, vol. 148, pp. 113-137 (1999).
Hansen, C.M., "The Three Dimensional Solubility Parameter—Key to Paint Component Affinities: I. Solvents, Plasticizers, Polymers, and Resins", Journal of Paint Technology, vol. 39, No. 505, pp. 104-117 (1967).
HCAPLUS abstract 1964: 70247, abstracting: Develop. Ind. Microbiol., vol. 2, pp. 47-53 (1961).
International Search Report for PCT Application No. PCT/FR03/02849, dated Jun. 24, 2004.
International Search Report for PCT/FR03/002844 (Priority Application for U.S. Appl. No. 10/529,318), dated May 14, 2005.
International Search Report for PCT/FR03/002847 (Priority Application for U.S. Appl. No. 10/529,266), dated May 17, 2004.
International Search Report for PCT/FR03/02841, dated Jun. 1, 2004.
International Search Report for PCT/FR03/02842 (Priority Application for U.S. Appl. No. 10/529,218), dated May 17, 2004.
International Search Report for PCT/FR03/02843 (Priority Application for U.S. Appl. No. 10/528,698), dated May 17, 2004.
International Search Report for PCT/FR03/02845 (Priority Application for U.S. Appl. No. 10/529,264), dated May 17, 2004.
International Search Report for PCT/FR03/02846 (Priority Application for U.S. Appl. No. 10/528,699), dated May 17, 2004.
International Search Report for PCT/FR03/02848 (Priority Application for U.S. Appl. No. 10/528,835), dated May 17, 2004.
International Search Report for PCT/IB2005/000230, dated May 27, 2005.
International Search Report for PCT/IB2005/000236, dated Aug. 3, 2005.
Kirk-Othmer, "Encyclopedia of Chemical Technology", vol. 22, 3rd Edition, Wiley, 1979, pp. 333-432.
Nojima. S., "Melting Behavior of Poly (E-caprolactone)-block-polybutadiene Copolymers", Macromolecules, 32, 3727-3734 (1999).
Office Action mailed Aug. 12, 2005, in co-pending U.S. Appl. No. 10/670,478.
Office Action mailed Aug. 12, 2009 in co-pending U.S. Appl. No. 10/949,448.
Office Action mailed Aug. 18, 2009 in co-pending U.S. Appl. No. 10/529,264.
Office Action mailed Dec. 10, 2008, in co-pending U.S. Appl. No. 10/528,698.
Office Action mailed Dec. 23, 2008, in co-pending U.S. Appl. No. 10/529,266.
Office Action mailed Jan. 7, 2008, in co-pending U.S. Appl. No. 10/670,388.
Office Action mailed Jun. 12, 2009 in co-pending U.S. Appl. No. 11/086,906.
Office Action mailed Jun. 24, 2009 in co-pending U.S. Appl. No. 10/528,698.
Office Action mailed Jun. 24, 2009 in co-pending U.S. Appl. No. 10/529,267.
Office Action mailed Jun. 29, 2009 in co-pending U.S. Appl. No. 10/529,266.
Office Action mailed Jun. 4, 2009 in co-pending U.S. Appl. No. 10/670,478.
Office Action mailed Mar. 12, 2009, in co-pending U.S. Appl. No. 10/529,218.
Office Action mailed Mar. 18, 2009, in co-pending U.S. Appl. No. 10/528,699.
Office Action mailed Mar. 18, 2009, in co-pending U.S. Appl. No. 10/573,579.
Office Action mailed Mar. 26, 2008, in co-pending U.S. Appl. No. 10/670,478.
Office Action mailed Mar. 7, 2006, in co-pending U.S. Appl. No. 10/670,478.
Office Action mailed May 3, 2007, in co-pending U.S. Appl. No. 10/670,478.
Office Action mailed Nov. 15, 2006, in co-pending U.S. Appl. No. 10/670,478.
Office Action mailed Nov. 17, 2009 in co-pending U.S. Appl. No. 10/528,835.
Office Action mailed Nov. 25, 2008, in co-pending U.S. Appl. No. 10/949,448.
Office Action mailed Nov. 25, 2008, in co-pending U.S. Appl. No. 10/670,388.
Office Action mailed Oct. 1, 2008, in co-pending U.S. Appl. No. 10/529,318.
Office Action mailed Oct. 21, 2008, in co-pending U.S. Appl. No. 10/670,478.
Office Action mailed Oct. 27, 2009 in co-pending U.S. Appl. No. 10/529,218.
Office Action mailed Sep. 2, 2009 in co-pending U.S. Appl. No. 10/529,318.
Office Action mailed Sep. 28, 2009 in co-pending U.S. Appl. No. 10/670,478.
Office Action mailed Sep. 7, 2007, in co-pending U.S. Appl. No. 10/670,478.
Pigeon, R. et al., Chimie Macromoleculaire Appliquee, No. 600, 40/41 (1974), pp. 139-158.
Prince, L.M. ed., Macroemulsions Theory and Practice, Academic Press (1977), pp. 21-32.
Rangarajan P., et al., "Morphology of Semi-Crystalline Block Copolymers of Ethylene-(ethylene-alt-propylene)," Macromolecules, 26, 4640-4645 (1993).
Richter, P. et al., "Polymer Aggregates with Crystalline Cores: The System Poly(ethylene)-poly(ethylene-propylene)," Macromolecules, 30, 1053-1068 (1997).
Co-pending U.S. Appl. No. 10/949,435, filed Sep. 27, 2004; Inventors: Xavier Blin et al.
Co-pending U.S. Appl. No. 11/878,067, filed Jul. 20, 2007; Inventors: Caroline Lebre et al.
Co-pending U.S. Appl. No. 11/878,849, filed Jul. 27, 2007; Inventors: Celine Farcet et al.
Cortazar, M. et al., "Glass Transition Temperatures of Plasticized Polyarylate,", Polymer Bulletin 18, 149-154 (1987).
English language Abstract of EP 1 518 535, dated Mar. 30, 2005.
English language Abstract of EP 1 604 634, dated Dec. 14, 2005.
English language Abstract of FR 1 222 944, dated Jun. 14, 1960.
English language Abstract of FR 1 564 110, dated Jan. 1968.
English language Abstract of FR 2 357 241, dated Feb. 3, 1978.
English language Abstract of FR 2 880 268, dated Jul. 7, 2006.
English language Abstract of JP 2003-40336, Feb. 13, 2003.
English language Abstract of JP 2006-151867, dated Jun. 15, 2006.
Erichsen et al., "Molecular Weight Dependence of the Surface Glass Transition of Polystyrene Films Investigated by the Embedding of Gold Nanoclusters," MRS Publication, 2001.
French Search Report for FR 04/03088, dated Nov. 2, 2004.
French Search Report for FR 06/53144, dated Feb. 13, 2007.
French Search Report for FR 06/53154, dated Apr. 2, 2007.
Nojiri et al., "Molecular Weight Dependence of the Glass Transition Temperature in Poly(vinyl acetate)," Japan J. Appl. Phys. 10 (1971), p. 803.
Specific Gravity and Viscosity of Liquid Table; available at http://www.csgnetwork.com/sgvisc.html. Sesame seed oil information originally published Mar. 28, 2002.
Toniu et al., "Process for Preparation of Block Polymers, Products Obtained by Means of the Process and Cosmetic Compositions Containing Them", 1973, French Patent Office, pp. 1-26 (English translation of French Patent No. FR2140977).
Notice of Allowance in U.S. Appl. No. 10/670,478 dated Jul. 6, 2010.
Office Action mailed Apr. 28, 2010, in co-pending U.S. Appl. No. 10/528,835.
Office Action mailed Aug. 2, 2010, in co-pending U.S. Appl. No. 10/949,435.
Office Action mailed Aug. 31, 2010, in co-pending U.S. Appl. No. 10/529,265.
Office Action mailed Dec. 29, 2009 in co-pending U.S. Appl. No. 10/529,265.
Office Action mailed Dec. 3, 2009 in co-pending U.S. Appl. No. 10/528,698.

(56) References Cited

OTHER PUBLICATIONS

Office Action mailed Feb. 2, 2010, in co-pending U.S. Appl. No. 10/949,448.
Office Action mailed Feb. 27, 2009, in co-pending U.S. Appl. No. 11/878,849.
Office Action mailed Jan. 28, 2010, in co-pending U.S. Appl. No. 10/529,264.
Office Action mailed Jul. 12, 2010, in co-pending U.S. Appl. No. 11/858,994.
Office Action mailed Jul. 21, 2009, in co-pending U.S. Appl. No. 11/878,067.
Office Action mailed Jul. 28, 2010, in co-pending U.S. Appl. No. 10/529,264.
Office Action mailed Jul. 9, 2010, in co-pending U.S. Appl. No. 11/859,004.
Office Action mailed Jul. 9, 2010, in co-pending U.S. Appl. No. 11/859,015.
Office Action mailed Mar. 17, 2010, in co-pending U.S. Appl. No. 10/529,318.
Office Action mailed Mar. 18, 2009, in related U.S. Appl. No. 11/089,172.
Office Action mailed Mar. 30, 2010, in co-pending U.S. Appl. No. 11/878,067.
Office Action mailed May 12, 2010, in co-pending U.S. Appl. No. 11/086,906.
Office Action mailed May 28, 2010, in co-pending U.S. Appl. No. 10/573,579.
Office Action mailed Nov. 6, 2009 in co-pending U.S. Appl. No. 10/949,435.
Office Action mailed Sep. 9, 2009, in co-pending U.S. Appl. No. 11/878,849.
Related U.S. Appl. No. 11/089,172, filed Mar. 25, 2005, Inventors: Katarina Benabdillah et al.

* cited by examiner

STYLING COMPOSITION COMPRISING, IN A PREDOMINANTLY AQUEOUS MEDIUM, A PSEUDO-BLOCK POLYMER, PROCESSES EMPLOYING SAME AND USES THEREOF

This application claims the benefit of U.S. Provisional Application No. 60/571,925, filed May 18, 2004, which is hereby incorporated by reference.

Disclosed herein are styling cosmetic compositions comprising, in a cosmetically acceptable medium predominantly comprising water, at least one pseudo-block polymer. The disclosure also provides processes for shaping and/or holding hairstyles, in which the compositions are employed, and to the uses of the compositions.

The cosmetic compositions for shaping and/or holding the hairstyle that are the most widely available on the cosmetics market are spray compositions comprising a solution, usually an alcoholic solution, and at least one component, known as fixing components, which are generally random polymer resins whose function is to form welds between the hairs. These fixing components may often be formulated as a mixture with various cosmetic adjuvants. The cosmetic compositions may generally be packaged either in a suitable aerosol container pressurized using a propellant, or in a pump-dispenser bottle.

Aerosol systems for fixing hair may comprise a liquid phase (or fluid) and a propellant. The liquid phase may comprise the fixing components and a suitable solvent.

Once applied to the hair, the liquid phase dries, allowing the formation of welds required for the fixing of the hair by the fixing components. The welds should be rigid enough to hold the hairs, and should do so with a sufficient persistence of effects, such as moisture resistance. However, the welds should also be fragile enough for the user to be able, by combing or brushing the hair, to destroy them without injuring the scalp or damaging the hair. The cosmetic compositions should also be stable over time. At least one good cosmetic effect on the hair may also be sought, for example, softness and disentangling.

It is moreover sought to reduce the amount of volatile solvents present in these compositions, for environmental reasons. The total or partial replacement of the volatile solvents, such as alcohol, with water may generally be reflected by a reduction in fixing properties, the persistence of the styling effect over time and the cosmetic properties.

The present disclosure relates to pseudo-block polymers may be used to prepare predominantly aqueous styling compositions which are stable for several months and allow good fixing and good hold of the hair, i.e., a styling effect that persists throughout the day, or even for several days, with good moisture resistance, and which is easy to remove by shampooing. These compositions also make it possible to give the hair good cosmetic properties, such as softness or disentangling effects.

Furthermore, the compositions predominantly aqueous base makes it highly ecologically advantageous.

One embodiment of the present disclosure is a styling cosmetic composition comprising, in a cosmetically acceptable medium predominantly comprising water, at least one pseudo-block polymer.

Other embodiments of the disclosure are cosmetic treatment processes for shaping or holding a hairstyle, employing these cosmetic compositions.

Another embodiment of the disclosure relates to the uses of pseudo-block polymers in predominantly aqueous cosmetic compositions to obtain one or more properties chosen from fixing of the hair that is persistent over time, fixing of the hair that has good moisture resistance and good cosmetic properties.

Other subjects, characteristics, aspects and advantages of the embodiments disclosed herein will emerge even more clearly on reading the description and the examples that follow.

As used herein, the term "styling composition" means a composition for shaping and/or holding the hairstyle.

As used herein, the term "medium predominantly comprising water" means a medium comprising more than 50%, for example, more than 70% and, further, for example, more than 85% by weight of water, relative to the total weight of the at least one styling composition. In one embodiment, the medium comprises upwards of 99.9% by weight of water, relative to the total weight of the at least one styling composition.

The cosmetically acceptable medium is a medium comprising water and optionally at least one organic solvent.

As used herein, the term "organic solvent" means an organic compound with a molecular weight of less than 500, which is liquid at a temperature of 25° C. and at atmospheric pressure. In one embodiment, the organic compound is polar.

In one embodiment, the at least one organic solvent is an alcohol. For example, the at least organic solvent may be chosen from $C_1$-$C_4$ lower alcohols, such as ethanol, isopropanol, tert-butanol, and n-butanol; polyols, for example, propylene glycol, and polyol ethers, in one embodiment the alcohol is an ethanol.

In some embodiments, the compositions comprise less than 15% of organic solvents.

The at least one pseudo-block polymer used in the at least one styling composition disclosed herein is chosen from block polymers comprising at least one first block and at least one second block that are mutually incompatible and that have different glass transition temperatures (Tg), wherein the at least one first and the at least one second block are linked together via an intermediate segment comprising at least one constituent monomer of the at least one first block and at least one constituent monomer of the at least one second block, and wherein the at least one pseudo-block polymer has a polydispersity index (I) of greater than 2.

As used herein, the term "at least one block" means one or more blocks.

As used herein, the term "mutually incompatible blocks" means that the mixture formed from the polymer corresponding to the at least one first block and the polymer corresponding to the at least one second block is immiscible in the polymerization solvent that is of the majority amount by weight of the at least one pseudo-block polymer, at room temperature (25° C.) and atmospheric pressure ($10^5$ Pa), for a polymer mixture content of greater than or equal to 5% by weight, relative to the total weight of the mixture (polymers and solvent), wherein:

i) the polymers corresponding to the at least one first and at least one second blocks are present in the mixture in an amount such that the respective weight ratio ranges from 10:90 to 90:10 and ii) each of the polymers corresponding to the at least one first and at least one second blocks has an average (weight-average or number-average) molecular mass equal to that of the at least one pseudo-block polymer ±15%.

In the case wherein the polymerization solvent comprises a mixture of polymerization solvents, and in the event of two or more solvents present in identical mass proportions, the polymer mixture is immiscible in at least one of them.

Needless to say, in the case of a polymerization performed in only one solvent, this solvent is present in the majority amount.

The intermediate segment is a block comprising at least one constituent monomer of the first block and at least one constituent monomer of the second block of the polymer; it allows these blocks to be "compatibilized".

In one embodiment, the at least one pseudo-block polymer disclosed herein may be chosen from film-forming linear block ethylenic polymers.

As used herein, the term "ethylenic" polymer means a polymer obtained by polymerization of ethylenically unsaturated monomers.

As used herein, the term "block" polymer means a polymer comprising at least two different blocks, such as at least three different blocks.

The at least one pseudo-block polymer is a polymer of linear structure. In contrast, a polymer of non-linear structure is, for example, a polymer of branched, star or grafted structure, or the like.

As used herein, the term "film-forming" polymer means a polymer that is capable of forming by itself or in the presence of an auxiliary film-forming agent, a continuous film that adheres to a support, such as to keratin materials.

In some embodiments, the at least one pseudo-block polymer disclosed herein does not comprise any silicon atoms in its skeleton. As used herein, the term "skeleton" means the main chain of the polymer, as opposed to the pendent side chains.

In one embodiment, the at least one pseudo-block polymer disclosed herein is not water-soluble, i.e. the polymer is not soluble in water or mixtures of water and linear or branched lower monoalcohols comprising from 2 to 5 carbon atoms, such as ethanol, isopropanol or n-propanol, without pH modification, at an active material content of at least 1% by weight, at room temperature (25° C.).

In one embodiment, the at least one pseudo-block polymer disclosed herein is not an elastomer.

As used herein, the term "non-elastomeric polymer" means a polymer which, when it is subjected to a constraint intended to stretch it (for example by 30% relative to its initial length), does not return to a length substantially identical to its initial length when the constraint ceases.

More specifically, the term "non-elastomeric polymer" means a polymer with an instantaneous recovery $R_i$<50% and a delayed recovery $R_{2h}$<70% after having been subjected to a 30% elongation. For example, $R_i$ is <30% and $R_{2h}$<50%.

More specifically, the non-elastomeric nature of the at least one pseudo-block polymer used is determined according to the following protocol:

A polymer film is prepared by pouring a solution of the polymer in a Teflon-coated mould, followed by drying for 7 days in an environment conditioned at 23±5° C. and 50±10% relative humidity.

A film about 100 μm thick is thus obtained, from which are cut rectangular specimens (for example using a punch) 15 mm wide and 80 mm long.

This sample is subjected to a tensile stress using a machine sold under the reference Zwick, under the same temperature and humidity conditions as for the drying.

The specimens are pulled at a speed of 50 mm/min and the distance between the jaws is 50 mm, which corresponds to the initial length ($I_0$) of the specimen.

The instantaneous recovery $R_i$ is determined in the following manner:

the specimen is pulled by 30% ($\epsilon_{max}$), i.e. about 0.3 times its initial length ($I_0$)

the constraint is released by applying a return speed equal to the tensile speed, i.e. 50 mm/min, and the residual elongation of the specimen is measured as a percentage, after returning to zero constraint ($\epsilon_i$).

The percentage instantaneous recovery ($R_i$) is given by the following formula:

$$R_i = (\epsilon_{max} - \epsilon_i)/\epsilon_{max} \times 100$$

To determine the delayed recovery, the percentage residual elongation of the specimen ($\epsilon_{2h}$) is measured, 2 hours after returning to zero constraint.

The percentage delayed recovery ($R_{2h}$) is given by the following formula:

$$R_{2h} = (\epsilon_{max} - \epsilon_{2h})/\epsilon_{max} \times 100$$

Purely as a guide, a polymer according to one embodiment has an instantaneous recovery $R_i$ of 10% and a delayed recovery $R_{2h}$ of 30%.

For example, the at least one pseudo-block polymer used in the compositions disclosed herein comprises at least one first block and at least one second block that are mutually incompatible and that have different glass transition temperatures (Tg), wherein the at least one first and the at least one second block are linked together via an intermediate segment comprising at least one constituent monomer of the at least one first block and at least one constituent monomer of the at least one second block, wherein the at least one pseudo-block polymer has a polydispersity index (I) of greater than 2.

It is pointed out that, in the text hereinabove and hereinbelow, the terms "first block" and "second block" do not in any way condition the order of the blocks in the structure of the at least one pseudo-block polymer.

The polydispersity index (I) of the at least one pseudo-block polymer is equal to the ratio of the weight-average mass (Mw) to the number-average mass (Mn).

The weight-average molar mass (Mw) and number-average molar mass (Mn) are determined by gel permeation liquid chromatography (THF solvent, calibration curve established with linear polystyrene standards, refractometric detector).

The weight-average mass (Mw) of the at least one pseudo-block polymer used in the composition disclosed herein is, for example, less than or equal to 300,000; it ranges, for example, from 35,000 to 200,000, such as from 45,000 to 150,000.

The number-average mass (Mn) of the at least one pseudo-block polymer used in the composition disclosed herein is, for example, less than or equal to 70,000; it ranges, for example, from 10,000 to 60,000, such as from 12,000 to 50,000.

The polydispersity index of the polymer used in the compositions may be greater than or equal to 2, for example ranging from 2 to 9; greater than or equal to 2.5, for example, ranging from 2.5 to 8, or even greater than or equal to 2.8, for example, ranging from 2.8 to 6.

Each block of the at least one pseudo-block polymer used in the at least one styling composition disclosed herein is derived from one type of monomer or from several different types of monomers.

This means that each block may comprise a homopolymer or a copolymer; this copolymer constituting the block may in turn be random or alternating.

In some embodiments, the intermediate segment comprising at least one constituent monomer of the first block and at least one constituent monomer of the second block of the polymer is a random polymer.

The intermediate segment may be derived essentially from constituent monomers of the first block and of the second block.

As used herein, the term "essentially" means at least 85%, such as at least 90%, for example, at least 95% and, further, for example, 100%.

In another embodiment, the intermediate segment has a glass transition temperature Tg that is between the glass transition temperatures of the at least one first and at least one second blocks.

The at least one first and at least one second blocks have different glass transition temperatures.

The glass transition temperatures indicated for the at least one first and at least one second blocks may be theoretical Tg values determined from the theoretical Tg values of the constituent monomers of each of the blocks, which may be found in a reference manual such as the Polymer Handbook, 3rd Edition, 1989, John Wiley, according to the following relationship, known as Fox's law:

$$1/Tg = \sum_i (\overline{\omega}_i / Tg_i),$$

Wherein: $\overline{\omega}_i$ is the mass fraction of the monomer (i) in the block under consideration and $Tg_i$ is the glass transition temperature of the homopolymer of the monomer (i).

Unless otherwise indicated, the Tg values indicated for the at least one first and at least one second blocks disclosed herein are theoretical Tg values.

The difference between the glass transition temperatures of the at least one first and at least one second blocks may be greater than 10° C., for example, greater than 20° C. and, further, for example, greater than 30° C.

For example, the first block may be chosen from:
(a) a block with a Tg of greater than or equal to 40° C.,
(b) a block with a Tg of less than or equal to 20° C., and
(c) a block with a Tg of between 20 and 40° C.;
and the second block may be chosen from a category (a), (b) or (c) different from the first block.

(a) Block with a Tg of Greater than or Equal to 40° C.

The block with a Tg of greater than or equal to 40° C. has, for example, a Tg ranging from 40 to 150° C., such as greater than or equal to 50° C., for example, ranging from 50° C. to 120° C., and, further, such as from 50° C. to 100° C. and, further, such as greater than or equal to 60° C., for example, ranging from 60° C. to 120° C.

The block with a Tg of greater than or equal to 40° C. may be chosen from homopolymers and copolymers.

In the case where this block is a homopolymer, it is derived from monomers, which are such that the homopolymers prepared from these monomers have glass transition temperatures of greater than or equal to 40° C. This first block may be a homopolymer comprising only one type of monomer (for which the Tg of the corresponding homopolymer is greater than or equal to 40° C.).

In the case where the first block is a copolymer, it may be totally or partially derived from at least one monomer, the nature and concentration of which are chosen such that the Tg of the resulting copolymer is greater than or equal to 40° C. The copolymer may comprise, for example:
monomers which are such that the homopolymers prepared from these monomers have Tg values of greater than or equal to 40° C., for example, a Tg ranging from 40 to 150° C., such as greater than or equal to 50° C., for example, ranging from 50° C. to 120° C. and, further, such as greater than or equal to 60° C., for example, ranging from 60° C. to 120° C., and monomers which are such that the homopolymers prepared from these monomers have Tg values of less than 40° C., chosen from monomers with a Tg ranging from 20 to 40° C. and monomers with a Tg of less than or equal to 20° C., for example, a Tg ranging from −100 to 20° C., such as less than 15° C., further, for example, ranging from −80° C. to 15° C. and, further, such as less than 10° C., for example, ranging from −50° C. to 0° C., as described later.

The at least one monomer whose homopolymer has a glass transition temperature of greater than or equal to 40° C. is chosen, for example, from the following monomers, also known as main monomers:

methacrylates of formula $CH_2\!=\!C(CH_3)\!-\!COOR_1$
wherein $R_1$ is chosen from linear and branched unsubstituted alkyl groups comprising from 1 to 4 carbon atoms, such as a methyl, ethyl, propyl, and isobutyl groups or $R_1$ is chosen from $C_4$ to $C_{12}$ cycloalkyl groups;

acrylates of formula $CH_2\!=\!CH\!-\!COOR_2$
wherein $R_2$ is chosen from $C_4$ to $C_{12}$ cycloalkyl groups, such as an isobornyl group and a tert-butyl group; and (meth)acrylamides of formula:

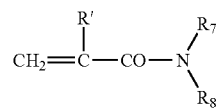

wherein $R_7$ and $R_8$, which may be identical or different, are each chosen from a hydrogen atom and linear and branched $C_1$ to $C_{12}$ alkyl groups, such as n-butyl, t-butyl, isopropyl, isohexyl, isooctyl, and isononyl groups; or $R_7$ is H and $R_8$ is a 1,1-dimethyl-3-oxobutyl group, and R' is chosen from H and methyl. Examples of monomers that may be mentioned include N-butylacrylamide, N-t-butylacrylamide, N-isopropylacrylamide, N,N-dimethylacrylamide, and N,N-dibutylacrylamide.

In some embodiments, the at least one monomer whose homopolymer has a glass transition temperature of greater than or equal to 40° C. may be chosen from methyl methacrylate, isobutyl (meth)acrylate and isobornyl (meth)acrylate.

(b) Block with a Tg of Less than or Equal to 20° C.

The block with a Tg of less than or equal to 20° C. has, for example, a Tg ranging from −100 to 20° C., for example, less than or equal to 15° C., such as ranging from −80° C. to 15° C. and, further, for example, less than or equal to 10° C., for example, ranging from −100° C. to 0° C., such as ranging from −50° C. to 0° C.

The block with a Tg of less than or equal to 20° C. may be chosen from homopolymer and copolymers.

In the case where this block is a homopolymer, it is derived from at least one monomer which is such that the homopolymer prepared from the at least one monomer has a glass transition temperatures of less than or equal to 20° C. This second block may be a homopolymer comprising only one type of monomer (for which the Tg of the corresponding homopolymer is less than or equal to 20° C.).

In the case where the block with a Tg of less than or equal to 20° C. is a copolymer, it may be totally or partially derived from at least one monomer, the nature and concentration of which are chosen such that the Tg of the resulting copolymer is less than or equal to 20° C.

It may comprise, for example at least one monomer whose corresponding homopolymer has a Tg of less than or equal to 20° C., for example, a Tg ranging from −100° C. to 20° C., such as less than 15° C., for example, ranging from −80° C. to 15° C. and, further, such as less than 10° C., for example, ranging from −50° C. to 0° C., and at least one monomer whose corresponding homopolymer has a Tg of greater than 20° C., such as monomers with a Tg of greater than or equal to 40° C., for example, a Tg ranging from 40 to 150° C., such as greater than or equal to 50° C., for example, ranging from 50° C. to 120° C. and, further, for example, greater than or equal to 60° C., even further, for example, ranging from 60° C. to 120° C. and/or monomers with a Tg ranging from 20 to 40° C., as described above.

In some embodiments, the block with a Tg of less than or equal to 20° C. is a homopolymer.

The at least one monomer whose homopolymer has a Tg of less than or equal to 20° C. may, for example, be chosen from the following monomers, or main monomers:

acrylates of formula $CH_2=CHCOOR_3$,
wherein $R_3$ is chosen from linear and branched $C_1$ to $C_{12}$ unsubstituted alkyl groups, with the exception of the tert-butyl group, wherein at least one hetero atom chosen from O, N and S is optionally intercalated;

methacrylates of the formula $CH_2=C(CH_3)-COOR_4$,
wherein $R_4$ is a linear or branched $C_6$ to $C_{12}$ unsubstituted alkyl group, wherein one or more heteroatoms chosen from O, N and S are optionally intercalated;

vinyl esters of formula $R_5-CO-O-CH=CH_2$,
wherein $R_5$ represents a linear or branched $C_4$ to $C_{12}$ alkyl group;

$C_4$ to $C_{12}$ alkyl vinyl ethers, $N-(C_4$ to $C_{12})$alkyl acrylamides, such as N-octylacrylamide, and mixtures thereof.

At least one of the main monomers that may be used for the block with a Tg of less than or equal to 20° C. may be chosen from alkyl acrylates whose alkyl chain comprises from 1 to 10 carbon atoms, with the exception of the tert-butyl group, such as methyl acrylate, isobutyl acrylate, 2-ethylhexyl acrylate.

(c) Block with a Tg Ranging from 20 to 40° C.

The block with a Tg ranging from 20 to 40° C. may be a homopolymer or a copolymer.

In the case where this block is a homopolymer, it is derived from at least one monomer (or main monomer) which is such that the homopolymer prepared from the at least one monomer has a glass transition temperature ranging from 20 to 40° C. This first block may be a homopolymer, comprising only one type of monomer (wherein the Tg of the corresponding homopolymer ranges from 20° C. to 40° C.).

The at least one monomer whose homopolymer has a glass transition temperature ranging from 20 to 40° C. may be chosen from n-butyl methacrylate, cyclodecyl acrylate, neopentyl acrylate and isodecylacrylamide.

In the case where the block with a Tg ranging from 20 to 40° C. is a copolymer, it is totally or partially derived from at least one monomer (or main monomer) whose nature and concentration is chosen such that the Tg of the resulting copolymer ranges from 20 to 40° C.

For example, the block with a Tg ranging from 20 to 40° C. may be chosen from copolymers totally or partially derived from:

main monomers whose corresponding homopolymer has a Tg of greater than or equal to 40° C., for example, a Tg ranging from 40° C. to 150° C., such as greater than or equal to 50° C., for example, ranging from 50 to 120° C. and, further, such as greater than or equal to 60° C., for example, ranging from 60° C. to 120° C., as described above, and main monomers whose corresponding homopolymer has a Tg of less than or equal to 20° C., for example, a Tg ranging from −100 to 20° C., such as less than or equal to 15° C., for example, ranging from −80° C. to 15° C. and, further, such as less than or equal to 10° C., for example, ranging from −50° C. to 0° C., as described above, wherein the monomers are chosen such that the Tg of the copolymer forming the first block ranges from 20 to 40° C.

Such main monomers may be chosen, for example, from at least one of methyl methacrylate, isobornyl acrylate and methacrylate, butyl acrylate, trifluoroethyl methacrylate, and 2-ethylhexyl acrylate.

In some embodiments, the proportion of the second block with a Tg of less than or equal to 20° C. ranges from 10% to 85% by weight, for example, from 20% to 70% and, even further, for example, from 20% to 50% by weight of the at least one pseudo-block polymer.

However, each of the blocks may contain in small proportion at least one constituent monomer of the other block.

Thus, the at least one first block may contain at least one constituent monomer of the at least one second block, and vice versa.

Each of the at least one first and/or at least one second blocks may comprise, in addition to the monomers indicated above, at least one other monomer known as at least one additional monomer, which are different from the main monomers mentioned above.

The nature and amount of the at least one additional monomer is chosen such that the block in which it is present has the desired glass transition temperature.

The additional monomer may be chosen, for example, from:

(a) hydrophilic monomers such as:

ethylenically unsaturated monomers comprising at least one carboxylic or sulfonic acid function, for example:

acrylic acid, methacrylic acid, crotonic acid, maleic anhydride, itaconic acid, fumaric acid, maleic acid, acrylamidopropanesulfonic acid, vinylbenzoic acid, vinylphosphoric acid, and salts thereof, ethylenically unsaturated monomers comprising at least one tertiary amine function, for example, 2-vinylpyridine, 4-vinylpyridine, dimethylaminoethyl methacrylate, diethylaminoethyl methacrylate, dimethylaminopropylmethacrylamide, and salts thereof, methacrylates of the formula $CH_2=C(CH_3)-COOR_6$, wherein $R_6$ is a linear or branched alkyl group having from 1 to 4 carbon atoms, such as a methyl, ethyl, propyl or isobutyl group, the alkyl group being substituted with one or more substituents chosen from hydroxyl groups (for example 2-hydroxypropyl methacrylate and 2-hydroxyethyl methacrylate) and halogen atoms (Cl, Br, I or F), such as trifluoroethyl methacrylate, methacrylates of the formula $CH_2=C(CH_3)-COOR_9$, $R_9$ is chosen from a linear or branched $C_6$ to $C_{12}$ alkyl group wherein one or more heteroatoms chosen from O, N and S are optionally intercalated, the alkyl group being substituted with one or more substituents chosen from hydroxyl groups and halogen atoms (e.g., Cl, Br, I or F);

acrylates of the formula $CH_2=CHCOOR_{10}$, wherein $R_{10}$ is chosen from a linear or branched $C_1$ to $C_{12}$ alkyl group substituted with one or more substituents chosen from hydroxyl groups and halogen atoms (e.g., Cl, Br, I or F), such as 2-hydroxypropyl acrylate and 2-hydroxyethyl acrylate; a $C_1$ to $C_{12}$ alkyl-O-POE (polyoxyethylene) with repetition of the oxyethylene unit 5 to 30 times, for example, methoxy-POE; and a polyoxyethylenated group comprising from 5 to 30 ethylene oxide units;

(b) ethylenically unsaturated monomers comprising one or more silicon atoms, such as methacryloxypropyltrimethoxysilane and methacryloxypropyltris(trimethylsiloxy)silane;

and mixtures thereof.

In some embodiments, the at least one additional monomer may be chosen from acrylic acid, methacrylic acid, and trifluoroethyl methacrylate.

According to one embodiment, the at least one pseudo-block polymer used in the at least one styling composition disclosed herein is a non-silicone polymer, i.e. a polymer free of silicon atoms.

The at least one additional monomer may be present in an amount less than or equal to 30% by weight, for example, from 1% to 30% by weight, further, for example, from 5% to 20% by weight and, even further, for example, from 7% to 15% by weight, relative to the total weight of the at least one first and/or at least one second blocks.

In some embodiments, each of the at least one first and at least one second blocks comprise at least one monomer chosen from (meth)acrylic acid esters and optionally at least one monomer chosen from (meth)acrylic acid.

For example, each of the at least one first and at least one second blocks may be totally derived from at least one monomer chosen from acrylic acid, (meth)acrylic acid esters and optionally from at least one monomer chosen from (meth)acrylic acid.

According to one embodiment, the at least one pseudo-block polymer used in the compositions disclosed herein is free of styrene. The term "polymer free of styrene" means a polymer comprising less than 10%, for example, less than 5%, further, for example, less than 2% and, even further, for example, less than 1% by weight, relative to the total weight of the polymer, of, or even comprises no, styrene monomeric units such as monomeric units of styrene and styrene derivatives, for instance methylstyrene, chlorostyrene, and chloromethylstyrene.

The at least one pseudo-block polymer used in the at least one styling composition disclosed herein may be obtained by free-radical solution polymerization according to the following preparation process:

a portion of the polymerization solvent is introduced into a suitable reactor and heated until the adequate temperature for the polymerization is reached (typically in the range from 60 to 120° C.), once the temperature for the polymerization is reached, the constituent monomers of the first block are introduced in the presence of some of the polymerization initiator, after a time T corresponding to a maximum degree of conversion of 90%, the constituent monomers of the second block and the rest of the initiator are introduced, the mixture is left to react for a time T' (ranging from 3 to 6 hours), after which the mixture is cooled to room temperature, and the polymer dissolved in the polymerization solvent is obtained.

As used herein, the term "polymerization solvent" means a solvent or a mixture of solvents. The polymerization solvent may be chosen, for example, from at least one of ethyl acetate, butyl acetate, alcohols such as isopropanol and ethanol, and aliphatic alkanes, such as isododecane. According to one embodiment, the polymerization solvent is a mixture of butyl acetate and isopropanol or isododecane.

First Embodiment

According to one embodiment, the at least one pseudo-block polymer used in the compositions disclosed herein comprises at least one (such as one) first block with a Tg of greater than or equal to 40° C., as described above in a) and at least one (such as one) second block with a Tg of less than or equal to 20° C., as described above in b).

For example, the at least one first block with a Tg of greater than or equal to 40° C. is a copolymer derived from at least one monomer which is such that the homopolymer prepared from the at least one monomer has a glass transition temperature of greater than or equal to 40° C., such as the monomers described above.

For example, the second block with a Tg of less than or equal to 20° C. is a homopolymer derived from at least one monomer which is such that the homopolymer prepared from the at least one monomer has a glass transition temperature of less than or equal to 20° C., such as the monomers described above.

For example, the proportion of the block with a Tg of greater than or equal to 40° C. ranges from 20% to 90%, further, for example, from 30% to 80% and even, further, for example, from 50% to 70% by weight of the polymer.

For example, the proportion of the block with a Tg of less than or equal to 20° C. ranges from 5% to 75%, for example, from 15% to 50% and, further, for example, from 25% to 45% by weight of the polymer.

Thus, according to a first variant, the polymer used in the compositions comprises:

a first block with a Tg of greater than or equal to 40° C., for example, having a Tg ranging from 70 to 110° C., which is a methyl methacrylate/acrylic acid copolymer, a second block with a Tg of less than or equal to 20° C., for example, ranging from 0 to 20° C., which is a methyl acrylate homopolymer, and an intermediate segment that is a methyl methacrylate/acrylic acid/methyl acrylate copolymer.

According to a second variant, the polymer used in the compositions comprises:

a first block with a Tg of greater than or equal to 40° C., for example, ranging from 70 to 100° C., which is a methyl methacrylate/acrylic acid/trifluoroethyl methacrylate copolymer, a second block with a Tg of less than or equal to 20° C., for example, ranging from 0 to 20° C., which is a methyl acrylate homopolymer, and an intermediate segment that is a methyl methacrylate/acrylic acid/methyl acrylate/trifluoroethyl methacrylate random copolymer.

According to a third variant, the polymer used in the compositions comprises:

a first block with a Tg of greater than or equal to 40° C., for example, ranging from 85 to 115° C., which is an isobornyl acrylate/isobutyl methacrylate copolymer, a second block with a Tg of less than or equal to 20° C., for example, ranging from −85 to −55° C., which is a 2-ethylhexyl acrylate homopolymer, and an intermediate segment, which is an isobornyl acrylate/isobutyl methacrylate/2-ethylhexyl acrylate random copolymer.

According to a fourth variant, the polymer used in the compositions comprises:

a first block with a Tg of greater than or equal to 40° C., for example, ranging from 85 to 115° C., which is an isobornyl acrylate/methyl methacrylate copolymer, a second block with a Tg of less than or equal to 20° C., for example, ranging from −85 to −55° C., which is a 2-ethylhexyl acrylate homopolymer, and an intermediate segment that is an isobornyl acrylate/methyl methacrylate/2-ethylhexyl acrylate random copolymer.

According to a fifth variant, the polymer used in the compositions comprises:

a first block with a Tg of greater than or equal to 40° C., for example, ranging from 95 to 125° C., which is an isobornyl acrylate/isobornyl methacrylate copolymer, a second block with a Tg of less than or equal to 20° C., for example, ranging from −85 to −55° C., which is a 2-ethylhexyl acrylate homopolymer, and an intermediate segment that is an isobornyl acrylate/isobornyl methacrylate/2-ethylhexyl acrylate random copolymer.

According to a sixth variant, the polymer used in the compositions comprises:

a first block with a Tg of greater than or equal to 40° C., for example, ranging from 85 to 115° C., which is an isobornyl methacrylate/isobutyl methacrylate copolymer, a second block with a Tg of less than or equal to 20° C., for example, ranging from −35 to −5° C., which is an isobutyl acrylate homopolymer, and an intermediate segment that is an isobornyl methacrylate/isobutyl methacrylate/isobutyl acrylate random copolymer.

According to a seventh variant, the polymer used in the compositions comprises:

a first block with a Tg of greater than or equal to 40° C., for example, ranging from 95 to 125° C., which is an isobornyl acrylate/isobornyl methacrylate copolymer, a second block with a Tg of less than or equal to 20° C., for example, ranging from −35 to −5° C., which is an isobutyl acrylate homopolymer, and an intermediate segment that is an isobornyl acrylate/isobornyl methacrylate/isobutyl acrylate random copolymer.

According to an eighth variant, the polymer used in the compositions comprises:

a first block with a Tg of greater than or equal to 40° C., for example, ranging from 60 to 90° C., which is an isobornyl acrylate/isobutyl methacrylate copolymer, a second block with a Tg of less than or equal to 20° C., for example, ranging from −35 to −5° C., which is an isobutyl acrylate homopolymer, and an intermediate segment that is an isobornyl acrylate/isobutyl methacrylate/isobutyl acrylate random copolymer.

According to a ninth variant, the polymer used in the compositions comprises:

a first block with a Tg of greater than or equal to 40° C., for example, with a Tg ranging from 70 to 110° C., which is an acrylic acid/methyl acrylate copolymer, a second block with a Tg of less than or equal to 20° C., for example, ranging from 0 to 20° C., which is a methyl acrylate homopolymer, and an intermediate segment that is an acrylic acid/methyl acrylate/polymethyl acrylate copolymer.

Second Embodiment

According to a second embodiment, the polymer used in the compositions comprises at least one (e.g., one) first block with a glass transition temperature (Tg) ranging from 20 to 40° C., as described above in (c) and at least one (e.g., one) second block with a glass transition temperature of less than or equal to 20° C., as described above in (b) or a glass transition temperature of greater than or equal to 40° C., as described in (a) above.

The proportion of the first block with a Tg ranging from 20 to 40° C. may range from 10 to 85%, for example, from 30 to 80%, further for example, from 50 to 70%, by weight of the polymer.

When the second block is a block with a Tg of greater than or equal to 40° C., it may be present in a proportion ranging from 10 to 85%, for example, from 20 to 70%, further for example, from 30 to 70% by weight, of the polymer.

When the second block is a block with a Tg of less than or equal to 20° C., it may be present in a proportion ranging from 10 to 85%, for example, from 20 to 70%, further for example, from 20 to 50%, by weight of the polymer.

The first block with a Tg ranging from 20 to 40° C. may be a copolymer derived from monomers which are such that the corresponding homopolymer has a Tg of greater than or equal to 40° C., and from monomers which are such that the corresponding homopolymer has a Tg of less than or equal to 20° C.

The second block with a Tg of less than or equal to 20° C. or with a Tg of greater than or equal to 40° C. may be a homopolymer.

Thus, according to a first variant of this second embodiment, the polymer used in the compositions may comprise:

a first block with a Tg of between 20 and 40° C., for example, with a Tg ranging from 25 to 39° C., which is a copolymer comprising at least one methyl acrylate monomer, at least one methyl methacrylate monomer and at least one acrylic acid monomer, a second block with a Tg of greater than or equal to 40° C., for example, ranging from 85 to 125° C., which is a homopolymer comprising methyl methacrylate monomers, and an intermediate segment comprising at least one methyl acrylate or methyl methacrylate monomer, and an intermediate segment comprising methyl methacrylate, at least one acrylic acid monomer and at least one methyl acrylate monomer.

According to a second variant of this second embodiment, the polymer used in the compositions may comprise:

a first block with a Tg ranging from 20 to 40° C., for example, with a Tg ranging from 21 to 39° C., which is a copolymer comprising isobornyl acrylate/isobutyl methacrylate/2-ethylhexyl acrylate, a second block with a Tg of less than or equal to 20° C., for example, ranging from −65 to −35° C., which is a methyl methacrylate homopolymer, and an intermediate segment that is an isobornyl acrylate/isobutyl methacrylate/2-ethylhexyl acrylate random copolymer.

According to a third variant of this second embodiment, the polymer used in the compositions may comprise:

a first block with a Tg ranging from 20 to 40° C., for example, with a Tg ranging from 21 to 39° C., which is an isobornyl acrylate/methyl acrylate/acrylic acid copolymer, a second block with a Tg of greater than or equal to 40° C., for example, ranging from 85 to 115° C., which is an isobornyl acrylate homopolymer, and an intermediate segment that is an isobornyl acrylate/methyl acrylate/acrylic acid random copolymer.

The cosmetic composition may comprise the pseudo-block polymer or polymers in an amount ranging from 0.1 to 60% by weight, for example, from 0.5% to 50%, further for example, from 1% to 40% by weight, relative to the total weight of the composition.

The styling cosmetic composition may also contain at least one additive chosen from, for example, other non pseudo-block fixing polymers (additional fixing polymers); silicones in soluble, dispersed or microdispersed form; thickening polymers; gelling agents; nonionic, anionic, cationic and amphoteric surfactants; ceramides and pseudoceramides; vitamins and provitamins including panthenol, plant, animal, mineral and synthetic oils; waxes other than ceramides and pseudoceramides; water-soluble and liposoluble, silicone or non-silicone sunscreens; glycerol; permanent or temporary dyes; nacreous agents and opacifiers; sequestering agents; plasticizers; solubilizers; pH modifiers; mineral thickeners; antioxidants; hydroxy acids; penetrating agents; fragrances; fragrance solubilizers (peptizers); preserving agents; and anticorrosion agents.

These additives may be present in the cosmetic compositions in an amount ranging from 0 to 20% by weight relative to the total weight of the cosmetic composition.

A person skilled in the art will take care to select the optional additives and the amount thereof such that they do not harm the properties of the compositions.

According to one embodiment, the compositions may further comprise at least one additional cosmetic additive chosen from thickening polymers, gelling agents and surfactants.

In some embodiments, the compositions may comprise at least one thickening polymer, also known as a "rheology modifier."

The at least one rheology modifier may be chosen from, for example, fatty acid amides (e.g., coconut monoethanolamide or diethanolamide, and oxyethylenated carboxylic acid alkyl ether monoethanolamide), cellulose-based thickeners (hydroxyethylcellulose, hydroxypropylcellulose or carboxymethylcellulose), guar gum and its derivatives (hydroxypropyl guar), gums of microbial origin (xanthan gum or scleroglucan gum), acrylic acid or acrylamidopropanesulfonic acid crosslinked homopolymers or copolymers, and associative thickening polymers as described below.

Associative polymers are water-soluble polymers that are capable, in an aqueous medium, of reversibly associating with each other or with other molecules. Their chemical structure comprises hydrophilic zones and hydrophobic zones comprising at least one fatty chain. The associative polymers may be anionic, cationic, amphoteric or nonionic.

The concentration of associative polymers may range from about 0.01 to 10%, e.g. from 0.1% to 5%, by weight relative to the total weight of the composition.

Anionic associative polymers include:
(I) polymers comprising at least one hydrophilic unit and at least one fatty-chain allyl ether unit, e.g., polymer comprising hydrophilic units comprising ethylenic unsaturated anionic monomers, e.g., vinylcarboxylic acid, an acrylic acid, a methacrylic acid, and mixtures thereof, the fatty-chain allyl ether unit of which corresponds to the monomer of formula (XV):

wherein R' is chosen from H and CH$_3$, B is an ethyleneoxy radical, n is zero or an integer ranging from 1 to 100, R is a hydrocarbon-based radical chosen from alkyl, arylalkyl, aryl, alkylaryl and cycloalkyl radicals, having from 8 to 30 carbon atoms, e.g., 10 to 24 or 12 to 18 carbon atoms. In some embodiments, R' is H, n is 10, and R is a stearyl (C$_{18}$) radical, and (II) polymers comprising at least one olefinic carboxylic acid hydrophilic unit and at least one unsaturated carboxylic acid (C$_{10}$-C$_{30}$)alkyl ester hydrophobic unit.

Anionic associative polymers of this type are described and prepared, according to an emulsion polymerization process, in EP Patent No. 216,479.

Anionic associative polymers include polymers formed from 20 to 60% by weight of acrylic acid and/or of methacrylic acid, from 5 to 60% by weight of lower alkyl (meth)acrylates, from 2 to 50% by weight of fatty-chain allyl ether of formula (XV), and from 0 to 1% by weight of a crosslinking agent which is a well-known copolymerizable unsaturated polyethylenic monomer, for example, diallyl phthalate, allyl (meth)acrylate, divinylbenzene, (poly)ethylene glycol dimethacrylate, and methylenebisacrylamide.

In some embodiments, the polymers are crosslinked terpolymers of methacrylic acid, of ethyl acrylate and of polyethylene glycol (10 EO) stearyl alcohol ether (Steareth-10), such as those sold by Allied Colloids as SALCARE SC 80® and SALCARE SC 90®, which are aqueous 30% emulsions of a crosslinked terpolymer of methacrylic acid, of ethyl acrylate and of steareth-10 allyl ether (40/50/10).

In some embodiments, the polymers comprise unsaturated olefinic carboxylic acid hydrophilic units corresponding to the monomer of formula (XVI) below:

wherein R$_1$ is chosen from H, CH$_3$ and C$_2$H$_5$, for example, acrylic acid, methacrylic acid or ethacrylic acid units, and in which the hydrophobic unit of (C$_{10}$-C$_{30}$)alkyl ester of unsaturated carboxylic acid type corresponds to the monomer of formula (XVII) below:

wherein R$_2$ is chosen from H, CH$_3$ and C$_2$H$_5$ (e.g., acrylate, methacrylate or ethacrylate units), for example, H (acrylate units) and CH$_3$ (methacrylate units), R$_3$ is a C$_{10}$-C$_{30}$, e.g., C$_{12}$-C$_{22}$ alkyl radical.

(C$_{10}$-C$_{30}$) alkyl esters of unsaturated carboxylic acids include, for example, lauryl acrylate, stearyl acrylate, decyl acrylate, isodecyl acrylate and dodecyl acrylate, and corresponding methacrylates, lauryl methacrylate, stearyl methacrylate, decyl methacrylate, isodecyl methacrylate, and dodecyl methacrylate.

Anionic polymers of this type are described and prepared, for example, as described in U.S. Pat. Nos. 3,915,921 and 4,509,949.

Anionic associative polymers that may be used include polymers formed from a monomer mixture comprising:
(i) acrylic acid,
(ii) an ester of formula (XVII) as described above wherein R$_2$ is chosen from H and CH$_3$ and R$_3$ is an alkyl radical having from 12 to 22 carbon atoms, and
(iii) a crosslinking agent, which is a well-known copolymerizable unsaturated polyethylenic monomer, for example, diallyl phthalate, allyl (meth)acrylate, divinylbenzene, (poly)ethylene glycol dimethacrylate and methylenebisacrylamide.

Anionic associative polymers that may be used include those comprising from 95 to 60% by weight of acrylic acid (hydrophilic unit), 4 to 40% by weight of $C_{10}$-$C_{30}$ alkyl acrylate (hydrophobic unit), and 0 to 6% by weight of crosslinking polymerizable monomer, or alternatively those comprising from 96 to 98% by weight of acrylic acid (hydrophilic unit), 1% to 4% by weight of $C_{10}$-$C_{30}$ alkyl acrylate (hydrophobic unit), and 0.1% to 0.6% by weight of crosslinking polymerizable monomer such as those described above.

Examples of the polymers above include products sold by Goodrich under the trade names PEMULEN TR1®, PEMULEN TR2® and CARBOPOL 1382®, for example, PEMULEN TR1', and the product sold by Seppic under the name COATEX SX®.

(III) maleic anhydride/$C_{30}$-$C_{38}$ α-olefin/alkyl maleate terpolymers, such as the product (maleic anhydride/$C_{30}$-$C_{38}$ α-olefin/isopropyl maleate copolymer) sold under the name PERFORMA V 1608® by Newphase Technologies.

(IV) acrylic terpolymers comprising:
(a) about 20 to 70% by weight of a carboxylic acid having α,β-monoethylenic unsaturation,
(b) about 20 to 80% by weight of a non-surfactant monomer having α,β-monoethylenic unsaturation other than (a), and
(c) about 0.5% to 60% by weight of a nonionic monourethane which is the product of reaction of a monohydric surfactant with a monoisocyanate having monoethylenic unsaturation,
such as those described in EP Patent Application No. 173,109 A, for example, the terpolymer described in Example 3, namely a methacrylic acid/methyl acrylate/behenyl alcohol dimethyl-meta-isopropenylbenzylisocyanate ethoxylated (40 EO) terpolymer, as an aqueous 25% dispersion.

(V) copolymers comprising carboxylic acid monomers having α,β-monoethylenic unsaturation, an ester of a carboxylic acid having α,β-monoethylenic unsaturation and of an oxyalkylenated fatty alcohol.

These compounds may also comprise as monomer an ester of a carboxylic acid having α,β-monoethylenic unsaturation and of a $C_1$-$C_4$ alcohol.

An example of a compound of this type is ACULYN 22® sold by Rohm & Haas, which is a methacrylic acid/ethyl acrylate/stearyl methacrylate oxyalkylenated terpolymer.

Associative polymers of the cationic type include:
(I) cationic associative polyurethanes, the family of which has been described by Applicants in French Patent Application No. 00/09609, which may be represented by the general formula (XVIII) below:

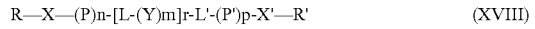

R—X—(P)n-[L-(Y)m]r-L'-(P')p-X'—R'  (XVIII)

wherein R and R', which may be identical or different, are chosen from a hydrophobic group and a hydrogen atom;
X and X', which may be identical or different, are chosen from a group comprising an amine function optionally bearing a hydrophobic group, or alternatively a group L";
L, L' and L", which may be identical or different, are chosen from a group derived from a diisocyanate;
P and P', which may be identical or different, are chosen from a group comprising an amine function optionally bearing a hydrophobic group;
Y is a hydrophilic group;

r is an integer ranging from 1 to 100, for example, from 1 to 50 or from 1 to 25; and
n, m and p each range, independently of each other, from 0 to 1000; and the molecule comprising at least one protonated or quaternized amine function and at least one hydrophobic group.

In one embodiment of these polyurethanes, the only hydrophobic groups are the groups R and R' at the chain ends.

One family of cationic associative polyurethanes that may be used is the family corresponding to formula (XVIII) described above wherein:
R and R' both independently are a hydrophobic group,
X and X' each are a group L",
n and p each range from 1 to 1000, and
L, L', L", P, P', Y, r and m are as described above.

Another family of cationic associative polyurethanes is the family corresponding to formula (XVIII) above wherein:
R and R' each independently represent a hydrophobic group,
X and X' each represent a group L",
n and p are each 0, and
L, L', L", Y, r and m have the meaning given above.

When n and p are 0 means that these polymers do not comprise units derived from a monomer comprising an amine function incorporated into the polymer during the polycondensation. The protonated amine functions of these polyurethanes result from the hydrolysis of excess isocyanate functions, at the chain end, followed by alkylation of the primary amine functions formed with alkylating agents comprising a hydrophobic group, i.e., compounds of the type RQ or R'Q, in which R and R' are as defined above and Q denotes a leaving group such as a halide, a sulfate, etc.

Another preferred family of cationic associative polyurethanes that may be used is the family corresponding to formula (Ia) above wherein:
R and R' are each independently chosen from a hydrophobic group,
X and X' each independently a group comprising a quaternary amine,
n and p are each zero, and
L, L', Y, r and m have the meaning given above.

The number-average molecular mass of the cationic associative polyurethanes may range from 400 to 500,000, for example, from 1000 to 400,000 and further from 1000 to 300,000.

As used herein, the term "hydrophobic group" means a radical or polymer comprising a saturated or unsaturated, linear or branched hydrocarbon-based chain, which may contain one or more heteroatoms such as P, O, N or S, or a radical comprising a perfluoro or silicone chain. When the hydrophobic group denotes a hydrocarbon-based radical, it comprises at least 10 carbon atoms, e.g., from 10 to 30 carbon atoms, for example, from 12 to 30 carbon atoms and further, for example, from 18 to 30 carbon atoms.

The hydrocarbon-based group may be derived from a monofunctional compound.

By way of example, the hydrophobic group may be derived from a fatty alcohol such as stearyl alcohol, dodecyl alcohol or decyl alcohol. It may also denote a hydrocarbon-based polymer such as, for example, polybutadiene.

When X and/or X' denote a group comprising a tertiary or quaternary amine, X and/or X' may be chosen from one of the following formulae:

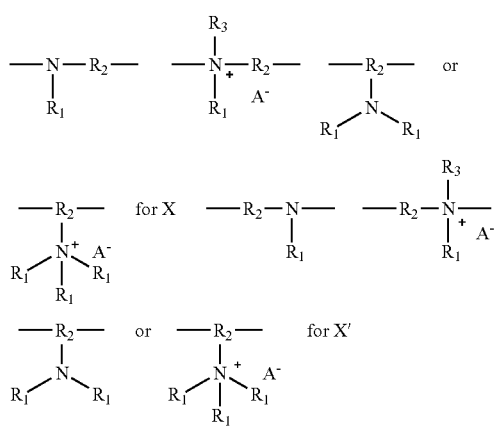

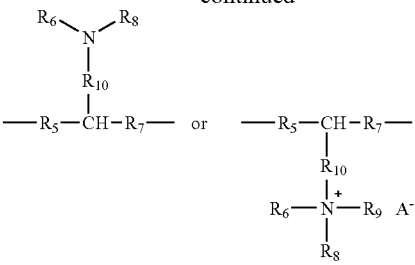

wherein:

$R_2$ is chosen from linear or branched alkylene radicals having from 1 to 20 carbon atoms, optionally comprising a saturated or unsaturated ring and an arylene radical, one or more of the carbon atoms optionally being replaced with a heteroatom chosen from N, S, O and P;

$R_1$ and $R_3$, which may be identical or different, are chosen from a linear or branched $C_1$-$C_{30}$ alkyl or alkenyl radicals or aryl radicals, at least one of the carbon atoms optionally being replaced with a heteroatom chosen from N, S, O and P;

$A^-$ is a physiologically acceptable counterion.

The groups L, L' and L" represent a group of the formula:

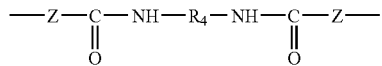

wherein:

Z is chosen from —O—, —S— and —NH—; and $R_4$ is chosen from linear or branched alkylene radicals having from 1 to 20 carbon atoms, optionally comprising a saturated or unsaturated ring, and an arylene radical, one or more of the carbon atoms optionally being replaced with a heteroatom chosen from N, S, O and P.

The groups P and P' comprising an amine function may be chosen from at least one of the following formulae:

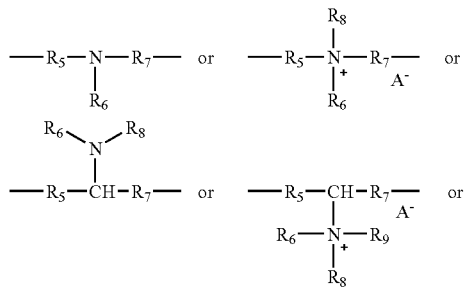

wherein:

$R_5$ and $R_7$ have the same meanings as $R_2$ defined above;

$R_6$, $R_8$ and $R_9$ have the same meanings as $R_1$ and $R_3$ defined above;

$R_{10}$ represents a linear or branched, optionally unsaturated alkylene group optionally comprising one or more heteroatoms chosen from N, O, S and P; and $A^-$ is a physiologically acceptable counterion.

With respect to the meaning of Y, the term "hydrophilic group" means a polymeric or non-polymeric water-soluble group.

When the hydrophilic compound is not a polymer, it may be, for example, ethylene glycol, diethylene glycol and propylene glycol.

When the hydrophilic compound is a hydrophilic polymer, it may be, for example, comprised of polyethers, sulfonated polyesters, sulfonated polyamides or a mixture of these polymers. The hydrophilic compound may be a polyether, for example, a poly(ethylene oxide) or poly(propylene oxide).

Cationic associative polyurethanes of formula (XVIII) that may be used are formed from diisocyanates and from various compounds with functions comprising a labile hydrogen. The functions comprising a labile hydrogen may be alcohol, primary or secondary amine or thiol functions, giving, after reaction with the diisocyanate functions, polyurethanes, polyureas and polythioureas, respectively. As used herein, the term "polyurethanes which can be used" encompasses these types of polymers, i.e., polyurethanes per se, polyureas, polythioureas, and copolymers thereof.

A first type of compound involved in the preparation of the polyurethane of formula (XVIII) is a compound comprising at least one unit comprising an amine function. This compound may be multifunctional, e.g., difunctional, i.e., it comprises two labile hydrogen atoms borne, for example, by a hydroxyl, primary amine, secondary amine or thiol function. A mixture of multifunctional and difunctional compounds in which the percentage of multifunctional compounds is low may also be used.

As mentioned above, this first type of compound, used to prepare the polyurethane of formula (XVIII) may comprise more than one unit comprising an amine function. In this case, it is a polymer bearing a repetition of the unit comprising an amine function.

Compounds of this type may be represented by one of the following formulae:

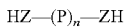

and

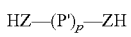

wherein Z, P, P', n and p are as defined above.

Examples of compounds comprising an amine function include N-methyldiethanolamine, N-tert-butyldiethanolamine and N-sulfoethyldiethanolamine.

The second compound involved in the preparation of the polyurethane of formula (XVIII) is a diisocyanate corresponding to the formula:

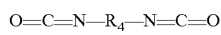

wherein $R_4$ is as defined above.

Examples include methylenediphenyl diisocyanate, methylenecyclohexane diisocyanate, isophorone diisocyanate, toluene diisocyanate, naphthalene diisocyanate, butane diisocyanate, and hexane diisocyanate.

A third compound involved in the preparation of the polyurethane of formula (XVIII) is a hydrophobic compound intended to form the terminal hydrophobic groups of the polymer of formula (XVIII).

This third compound comprises a hydrophobic group and of a function comprising a labile hydrogen, for example a hydroxyl, primary or secondary amine, or thiol function.

Examples include fatty alcohols such as stearyl alcohol, dodecyl alcohol and decyl alcohol. When this compound comprises a polymeric chain, it may be, for example, α-hydroxylated hydrogenated polybutadiene.

The hydrophobic group of the polyurethane of formula (XVIII) may also result from the quaternization reaction of the tertiary amine of the compound comprising at least one tertiary amine unit. Thus, the hydrophobic group may be introduced via a quaternizing agent. This quaternizing agent may be a compound of the formula RQ or R'Q, wherein R and R' are as defined above and Q denotes a leaving group such as a halide, a sulfate, etc.

The cationic associative polyurethane may also comprise a hydrophilic block. This block is provided by a fourth type of compound involved in the preparation of the polymer. This compound may be multifunctional, e.g., difunctional. It is also possible to use a mixture in which the percentage of multifunctional compound is low.

The functions comprising a labile hydrogen may be alcohol, primary or secondary amine or thiol functions. This compound may be a polymer terminated at the chain ends with one of these functions comprising a labile hydrogen.

Examples include ethylene glycol, diethylene glycol, and propylene glycol.

Examples of hydrophilic polymers include, for example, polyethers, sulfonated polyesters, sulfonated polyamides, and mixtures of these polymers. The hydrophilic compound may be a polyether, for example, a poly(ethylene oxide) or poly(propylene oxide).

The hydrophilic group termed Y in formula (XVIII) is optional. That is, the units comprising a quaternary amine or protonated function may suffice to provide the solubility or water-dispersibility required for this type of polymer in an aqueous solution.

Although the presence of the hydrophilic group Y is optional, cationic associative polyurethanes comprising such a group may be used.

(II) quaternized cellulose derivatives and polyacrylates comprising non-cyclic amine side groups.

The quaternized cellulose derivatives include:
quaternized celluloses modified with groups comprising at least one fatty chain, such as alkyl, arylalkyl or alkylaryl groups having at least 8 carbon atoms, and mixtures thereof; and
quaternized hydroxyethylcelluloses modified with groups comprising at least one fatty chain, such as alkyl, arylalkyl or alkylaryl groups having at least 8 carbon atoms, and mixtures thereof.

The alkyl radicals borne by the above quaternized celluloses or hydroxyethylcelluloses may have from 8 to 30 carbon atoms. Aryl radicals include phenyl, benzyl, naphthyl, and anthryl groups.

Examples of quaternized alkylhydroxyethylcelluloses comprising $C_8$-$C_{30}$ fatty chains include the products QUATRISOFT LM 200®, QUATRISOFT LM-X 529-18-A®, QUATRISOFT LM-X 529-18B® ($C_{12}$ alkyl) and QUATRISOFT LM-X 529-8® ($C_{18}$ alkyl) sold by Amerchol, and the products CRODACEL QM®, CRODACEL QL® ($C_{12}$ alkyl) and CRODACEL QS® ($C_{18}$ alkyl) sold by Croda.

Amphoteric associative polymers may be chosen from polymers comprising at least one non-cyclic cationic unit, for example, those prepared from or comprising from 1 to 20 mol %, for example, from 1.5 to 15 mol % and further, for example, from 1.5 to 6 mol % of fatty-chain monomer relative to the total number of moles of monomers.

Amphoteric associative polymers include polymers that are prepared by copolymerizing:

(1) at least one monomer of formula (XIX) or (XX):

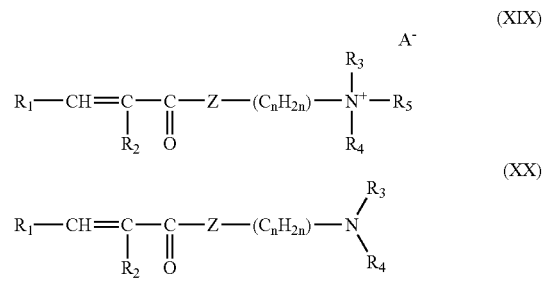

wherein $R_1$ and $R_2$, which may be identical or different, are chosen from a hydrogen atom and a methyl radical; $R_3$, $R_4$ and $R_5$, which may be identical or different, are each chosen from linear or branched alkyl radicals having from 1 to 30 carbon atoms, Z is chosen from an NH group and an oxygen atom, n is an integer ranging from 2 to 5, $A^-$ is an anion derived from an organic or mineral acid, such as a methosulfate anion or a halide such as chloride or bromide;

(2) at least one monomer of formula (XXI)

wherein $R_6$ and $R_7$, which may be identical or different, are chosen from hydrogen atoms and methyl radicals; and (3) at least one monomer of formula (XXII):

wherein $R_6$ and $R_7$, which may be identical or different, are chosen from hydrogen atoms or methyl radicals, X is chosen from an oxygen or nitrogen atom, and $R_8$ denotes a linear or branched alkyl radical having from 1 to 30 carbon atoms;

at least one of the monomers of formula (XIX), (XX) or (XXII) comprises at least one fatty chain.

The monomers of formulae (XIX) and (XX) may be chosen from, for example:

dimethylaminoethyl methacrylate, dimethylaminoethyl acrylate, diethylaminoethyl methacrylate, diethylaminoethyl acrylate, dimethylaminopropyl methacrylate, dimethylaminopropyl acrylate, dimethylaminopropylmethacrylamide, dimethylaminopropylacrylamide, these monomers optionally being quaternized, for example with a $C_1$-$C_4$ alkyl halide or a $C_1$-$C_4$ dialkyl sulfate.

For example, the monomer of formula (XIX) may be chosen from acrylamidopropyltrimethylammonium chloride and methacrylamidopropyltrimethylammonium chloride.

The monomers of formula (XXI) may be chosen from, for example, acrylic acid, methacrylic acid, crotonic acid and 2-methylcrotonic acid, e.g., acrylic acid.

The monomers of formula (XXII) may be chosen from $C_{12}$-$C_{22}$, for example, $C_{16}$-$C_{18}$ alkyl acrylates or methacrylates.

The monomers comprising the fatty-chain amphoteric polymers may be already neutralized and/or quaternized.

The ratio of the number of cationic charges/anionic charges may be equal to about 1.

The amphoteric associative polymers may comprise from 1 mol % to 10 mol % of the monomer comprising a fatty chain (monomer of formula (XIX), (XX) or (XXII)), for example, from 1.5 mol % to 6 mol %.

The weight-average molecular weights of the amphoteric associative polymers may range from 500 to 50,000,000, for example, from 10,000 to 5,000,000.

The amphoteric associative polymers may also comprise other monomers such as nonionic monomers, e.g., $C_1$-$C_4$ alkyl acrylates and methacrylates.

Amphoteric associative polymers are described and may be prepared, for example, as described in PCT Patent Application WO 98/44012.

Amphoteric associative polymers include acrylic acid/(meth)acrylamidopropyltrimethylammonium chloride/stearyl methacrylate terpolymers.

Nonionic associative polymers that may be used may be chosen from:

(1) celluloses modified with groups comprising at least one fatty chain; such as:
  hydroxyethylcelluloses modified with groups comprising at least one fatty chain, such as alkyl, arylalkyl or alkylaryl groups, or mixtures thereof, and in which the alkyl groups may be $C_8$-$C_{22}$ alkyl groups, for example, the product NATROSOL Plus GRADE 330 CS® ($C_{16}$ alkyls) sold by Aqualon, or the product BERMOCOLL EHM 100® sold by Berol Nobel,
  celluloses modified with alkylphenyl polyalkylene glycol ether groups, such as the product AMERCELL POLYMER HM-1500® (nonylphenyl polyethylene glycol (15) ether) sold by Amerchol,
(2) hydroxypropyl guars modified with groups comprising at least one fatty chain, such as the product ESAFLOR HM 22® ($C_{22}$ alkyl chain) sold by Lamberti, and the products RE210-18® ($C_{14}$ alkyl chain) and RE205-1® ($C_{20}$ alkyl chain) sold by Rhône-Poulenc,
(3) copolymers of vinylpyrrolidone and of fatty-chain hydrophobic monomers; examples include:
  the products ANTARON V216® and GANEX V216® (vinylpyrrolidone/hexadecene copolymer) sold by I.S.P.,
  the products ANTARON V220® and GANEX V220® (vinylpyrrolidone/eicosene copolymer) sold by the company I.S.P.,
(4) copolymers of $C_1$-$C_6$ alkyl methacrylates and acrylates and of amphiphilic monomers comprising at least one fatty chain, such as, for example, the oxyethylenated methyl acrylate/stearyl acrylate copolymer sold by Goldschmidt under the name ANTIL 208®,
(5) copolymers of hydrophilic methacrylates or acrylates and of hydrophobic monomers comprising at least one fatty chain, such as, for example, the polyethylene glycol methacrylate/lauryl methacrylate copolymer,
(6) polyurethane polyethers comprising in their chain both hydrophilic blocks usually of polyoxyethylenated nature and hydrophobic blocks which may be aliphatic sequences alone and/or cycloaliphatic and/or aromatic sequences,
(7) polymers with an aminoplast ether skeleton comprising at least one fatty chain, such as the PURE THIX® compounds sold by Sud-Chemie.

The polyurethane polyethers may comprise at least two hydrocarbon-based lipophilic chains having from 6 to 30 carbon atoms, separated by a hydrophilic block, the hydrocarbon-based chains optionally being pendent chains, or chains at the end of the hydrophilic block. It is possible for one or more pendent chains to be included. In addition, the polymer may comprise a hydrocarbon-based chain at one end or at both ends of a hydrophilic block.

The polyurethane polyethers may be multiblock, for example, in triblock form. Hydrophobic blocks may be at each end of the chain (for example: triblock copolymer with a hydrophilic central block) or distributed both at the ends and in the chain (for example: multiblock copolymer). These polymers may also be graft polymers or starburst polymers.

The nonionic fatty-chain polyurethane polyethers may be triblock copolymers in which the hydrophilic block is a polyoxyethylenated chain having from 50 to 1000 oxyethylene groups. The nonionic polyurethane polyethers comprise a urethane linkage between the hydrophilic blocks, whence arises the name.

Nonionic fatty-chain polyurethane polyethers also include those in which the hydrophilic blocks are linked to the lipophilic blocks via other chemical bonds.

Examples of nonionic fatty-chain polyurethane polyethers that may be used also include RHEOLATE 205® comprising a urea function, sold by Rheox, RHEOLATE® 208, 204 or 212, and ACRYSOL RM 184®.

The product ELFACOS T210® having a $C_{12-14}$ alkyl chain and the product ELFACOS T212® having a $C_{18}$ alkyl chain, from Akzo may also be used.

The product DW 1206B® from Rohm & Haas comprising a $C_{20}$ alkyl chain and a urethane linkage, sold at a solids content of 20% in water, may also be used.

It is also possible to use solutions or dispersions of these polymers, such as solutions in water or in aqueous-alcoholic medium. Examples of such polymers include RHEOLATE® 255, RHEOLATE® 278 and RHEOLATE® 244 sold by Rheox. The products DW 1206F and DW 1206J sold by Rohm & Haas may also be used.

Polyurethane polyethers that may be used include those described in the article by G. Fonnum, J. Bakke and F k. Hansen—Colloid Polym. Sci 271, 380.389 (1993).

Polyurethane polyethers that may be obtained by polycondensation of at least three compounds comprising (i) at least one polyethylene glycol having from 150 to 180 mols of ethylene oxide, (ii) stearyl alcohol or decyl alcohol, and (iii) at least one diisocyanate may also be used.

Such polyurethane polyethers are sold by Rohm & Haas under the names ACULYN 44® and ACULYN 46® [ACULYN 46® is a polycondensate of polyethylene glycol comprising 150 or 180 mols of ethylene oxide, of stearyl alcohol and of methylenebis(4-cyclohexyl isocyanate) (SMDI), at 15% by weight in a matrix of maltodextrin (4%) and water (81%); ACULYN 44® is a polycondensate of polyethylene glycol having 150 or 180 mols of ethylene oxide, of decyl alcohol and of methylenebis(4-cyclohexylisocyanate) (SMDI), at 35% by weight in a mixture of propylene glycol (39%) and water (26%)].

Non-associative gelling agents may also be used as thickeners. Included among these are polymers or copolymers of unsaturated carboxylic organic acids or of unsaturated esters, polysaccharide derivatives, gums, colloidal silicates, polyethylene glycols, polyvinyl pyrrolidones and hydrophilic silica gels.

The amount of thickeners present in the compositions may range from 0.01 to 10%, for example, from 0.1 to 5% by weight, relative to the total weight of the composition.

In some embodiments, the compositions further comprise at least one surfactant.

Suitable surfactants include:

(i) Anionic Surfactant(s):

Examples of anionic surfactants that may be used, alone or as mixtures, include, but are not limited to, salts (e.g., alkali metal salts, such as sodium salts, ammonium salts, amine salts, amino alcohol salts, and magnesium salts) of the following compounds: alkyl sulfates, alkyl ether sulfates, alkylamido ether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; ($C_6$-$C_{24}$)alkyl sulfosuccinates, ($C_6$-$C_{24}$)alkyl ether sulfosuccinates, ($C_6$-$C_{24}$)alkylamide sulfosuccinates; ($C_6$-$C_{24}$)alkyl sulfoacetates; ($C_6$-$C_{24}$)acyl sarcosinates; and ($C_6$-$C_{24}$)acyl glutamates. It is also possible to use ($C_6$-$C_{24}$) alkylpolyglycoside carboxylic esters such as alkylglucoside citrates, alkylpolyglycoside tartrates and alkylpolyglycoside sulfosuccinates, alkylsulfosuccinamates; acyl isethionates and N-acyl taurates. The alkyl or acyl radical of all of these different compounds may have from 12 to 20 carbon atoms and the aryl radical may be a phenyl or benzyl group. Anionic surfactants which may be used include fatty acid salts such as oleic, ricinoleic, palmitic and stearic acid salts, coconut oil acid or hydrogenated coconut oil acid; acyl lactylates in which the acyl radical has from 8 to 20 carbon atoms. It is also possible to use alkyl D-galactoside uronic acids and their salts, polyoxyalkylenated ($C_6$-$C_{24}$)alkyl ether carboxylic acids, polyoxyalkylenated ($C_6$-$C_{24}$)alkylaryl ether carboxylic acids, polyoxyalkylenated ($C_6$-$C_{24}$)alkylamido ether carboxylic acids and their salts, such as those having from 2 to 50 alkylene oxide groups, for example, ethylene oxide groups, and mixtures thereof.

(ii) Nonionic Surfactant(s):

Nonionic surfactants are compounds that are well known (see, for example, "Handbook of Surfactants" by M. R. Porter, published by Blackie & Son (Glasgow and London), 1991, pp. 116-178) and their nature is not a critical factor. Thus, they can be chosen from, for example, polyethoxylated or polypropoxylated, alkylphenols; and alphadiols or alcohols, having a fatty chain having, for example, 8 to 18 carbon atoms, it being possible for the number of ethylene oxide or propylene oxide groups to range from 2 to 50. Copolymers of ethylene oxide and of propylene oxide; condensates of ethylene oxide and of propylene oxide with fatty alcohols; polyethoxylated fatty amides preferably having from 2 to 30 mols of ethylene oxide, polyglycerolated fatty amides comprising on average from 1 to 5, e.g., from 1.5 to 4, glycerol groups; oxyethylenated fatty acid esters of sorbitan having from 2 to 30 mols of ethylene oxide; fatty acid esters of sucrose; fatty acid esters of polyethylene glycol; alkylpolyglycosides; N-alkylglucamine derivatives; and amine oxides such as ($C_{10}$-$C_{14}$)alkylamine oxides and N-acylaminopropylmorpholine oxides may also be used.

(iii) Amphoteric or Zwitterionic Surfactants:

The amphoteric or zwitterionic surfactants, the nature of which is not a critical factor, may be chosen from, for example, aliphatic secondary or tertiary amine derivatives in which the aliphatic radical is a linear or branched chain having from 8 to 18 carbon atoms and comprising at least one water-solubilizing anionic group (for example, carboxylate, sulfonate, sulfate, phosphate, and phosphonate); ($C_8$-$C_{20}$) alkylbetaines; sulfobetaines; ($C_8$-$C_{20}$)alkylamido($C_1$-$C_6$) alkylbetaines; or ($C_8$-$C_{20}$)alkylamido($C_1$-$C_6$)alkylsulfobetaines.

Amine derivatives that may be used include the products sold under the name MIRANOL, as described in U.S. Pat. Nos. 2,528,378 and 2,781,354 and classified in the CTFA dictionary, 3rd edition, 1982, under the names amphocarboxyglycinates and amphocarboxypropionates, with the respective structures:

wherein:

$R_2$ is chosen from alkyl radicals of an acid $R_2$—COOH present in hydrolyzed coconut oil, heptyl, nonyl or undecyl radicals, and $R_3$ is a beta-hydroxyethyl group and $R_4$ is a carboxymethyl group;

and

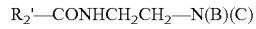

wherein:

B is —$CH_2CH_2OX'$, C is —$(CH_2)_n$—Y', and z is 1 or 2, X' is chosen from a —$CH_2CH_2$—COOH group and a hydrogen atom, Y' is chosen from —COOH and the —$CH_2$—CHOH—$SO_3H$ radical, $R_2'$ is chosen from alkyl radicals of an acid $R_9$-COOH present in coconut oil or in hydrolysed linseed oil, alkyl radicals, for example, a $C_7$, $C_9$, $C_{11}$ or $C_{13}$ alkyl radicals, a $C_{17}$ alkyl radical and its iso form, and unsaturated $C_{17}$ radicals.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid, and cocoamphodipropionic acid.

Examples include the cocoamphodiacetate sold under the trade name MIRANOL® C2M concentrate by Rhodia Chimie.

(iv) Cationic Surfactants:

Cationic surfactants include, but are not limited to, salts of optionally polyoxyalkylenated primary, secondary or tertiary fatty amines; quaternary ammonium salts such as tetraalkylammonium, alkylamidoalkyltrialkylammonium, trialkylbenzylammonium, trialkylhydroxyalkylammonium, and alkylpyridinium chlorides and bromides; imidazoline derivatives; and cationic amine oxides.

The amounts of surfactants present in the composition may range from 0.01 to 40%, for example, from 0.1% to –30%, by weight relative to the total weight of the composition.

The present disclosure also provides cosmetic processes for shaping and/or holding the hair, comprising the application to the hair of the compositions of the present disclosure, followed by optional rinsing and by drying.

Drying may take place in the open air or under the action of a heating device such as a hairdryer or a hood.

The present disclosure also relates to the use of the compositions selected from hair lotions, hair gels, hair mousses without gaseous propellants ("foamers"), hair creams or hairsprays in a pump flask without gaseous propellants, for the shaping and/or holding the hair.

The invention is illustrated in greater detail by the examples described below. Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters in the disclosure above are approximations, the numerical values set forth in the specific examples are reported as precisely as possible. Any numerical value, however, inherently contains certain errors necessarily resulting from the standard deviation found in its respective testing measurements.

EXAMPLE 1

Preparation of a Poly(Acrylic Acid/Methyl Acrylate) Pseudo-Block Polymer 100 g of butyl acetate was introduced into a 1 liter reactor and the temperature was then increased from room temperature (25° C.) to 90° C. in 1 hour.

30 g of acrylic acid, 30 g of methyl acrylate, 40 g of butyl acetate, 70 g of isopropanol and 1.8 g of 2,5-bis(2-ethylhexanoylperoxy)-2,5-dimethylhexane (TRIGONOX® 141 from Akzo Nobel) were then added, at 90° C. over 1 hour.

The mixture was maintained at 90° C. for 1 hour.

90 g of methyl acrylate, 70 g of butyl acetate, 20 g of isopropanol and 1.2 g of 2,5-bis(2-ethylhexanoylperoxy)-2,5-dimethylhexane were then introduced into the above mixture, at 90° C. and over 1 hour.

The mixture was maintained at 90° C. for 3 hours, then diluted with 105 g of butyl acetate and 45 g of isopropanol, and the mixture was then cooled.

A solution having 40% polymer active material in a butyl acetate/isopropanol mixture was obtained.

A polymer comprising a first poly(acrylic acid/methyl acrylate) block with a Tg of 80° C., a second polymethyl acrylate block with a Tg of 10° C. and an intermediate segment that was an acrylic acid/methyl acrylate/polymethyl acrylate random polymer was obtained.

The polymer had a weight-average mass of 50,000 g/mol and a number-average mass of 17,000, i.e., a polydispersity index I of 2.95.

The polymer had a glass transition temperature (Tg) of 49° C.

EXAMPLE 2

A composition according to the invention in the form of a styling lotion was prepared:

| Poly(acrylic acid/methyl acrylate) pseudo-block polymer | 2% AM |
|---|---|
| Ethanol | 5% AM |
| Demineralized water | qsp 100% |

Given as weight percentages.

EXAMPLE 3

A composition according to the invention in the form of a styling gel:

| Poly(acrylic acid/methyl acrylate) pseudo-block polymer | 4% AM |
|---|---|
| Jaguar HP105 (Rhodia) | 1% AM |
| Demineralized water | qsp 100% |

Given as weight percentages.

What is claimed is:

1. A styling cosmetic composition comprising, in a cosmetically acceptable medium comprising a pseudo-block polymer comprising a first poly(acrylic acid/methyl acrylate) block, a second polymethyl acrylate block, and an intermediate segment that is an acrylic acid/methyl acrylate/polymethyl acrylate random polymer block, wherein the styling cosmetic composition is a hair styling cosmetic composition that comprises more than 70% by weight of water relative to the total weight of the hair styling cosmetic composition.

2. The styling cosmetic composition according to claim 1, wherein the cosmetically acceptable medium comprises more than 85% by weight of water relative to the total weight of the composition.

3. The styling cosmetic composition according to claim 1, wherein the pseudo-block polymer is insoluble in water or in a mixture of water and linear or branched lower monoalcohols having from 2 to 5 carbon atoms, without pH modification, at an active material content of at least 1% by weight, at room temperature (25° C.).

4. The styling cometic composition according to claim 1, wherein the pseudo-block polymer is not an elastomer.

5. The styling cosmetic composition according to claim 1, wherein the pseudoblock polymer is a film-forming linear block polymer.

6. The styling cosmetic composition according to claim 1, further comprising a thickener.

7. The styling cosmetic composition according to claim 6, wherein the thickener is an associative thickening polymer.

8. The styling cosmetic composition according to claim 6, wherein the thickener is a gelling agent.

9. The styling cosmetic composition according to claim 6, wherein the thickener concentration ranges from 0.01 to 10% by weight relative to the total weight of the composition.

10. The styling cosmetic composition according to claim 6, wherein the thickener concentration ranges from 0.1 to 5% by weight relative to the total weight of the composition.

11. The styling cosmetic composition according to claim 1, further comprising a surfactant.

12. The styling cosmetic composition according to claim 11, wherein the surfactant concentration ranges from 0.01 to 40% by weight relative to the total weight of the composition.

13. The styling cosmetic composition according to claim 11, wherein the surfactant concentration ranges from 0.1 to 30% by weight relative to the total weight of the composition.

14. A cosmetic treatment process for shaping and/or holding a hairstyle, employing a composition comprising, in a cosmetically acceptable medium, a pseudo-block polymer comprising a first poly(acrylic acid/methyl acrylate) block, a second polymethyl acrylate block, and an intermediate segment that is an acrylic acid/methyl acrylate/polymethyl acrylate random polymer block, wherein the composition is a hair styling cosmetic composition that comprises more than 70% by weight of water relative to the total weight of the composition.

15. The cosmetic trearment process according to claim 14, wherein the shaping of the hair is persistent over time.

16. The cosmetic treatment process according to claim 14, wherein the shaping of the hair is moisture-resistant.

* * * * *